United States Patent
Park et al.

(10) Patent No.: US 11,422,120 B2
(45) Date of Patent: Aug. 23, 2022

(54) MOVING DEVICE FOR CONTAMINATION DETECTION, CONTAMINATION DETECTING SYSTEM AND METHOD, AND COMPUTER-READABLE RECORDING MEDIUM

(71) Applicant: HANWHA DEFENSE CO., LTD., Changwon-si (KR)

(72) Inventors: Jae Hyun Park, Changwon-si (KR); Ki Chong Kim, Changwon-si (KR); Byung Ki Kim, Changwon-si (KR); Tae Hyoung Kim, Changwon-si (KR)

(73) Assignee: HANWHA DEFENSE CO., LTD., Changwon-si (KR)

( * ) Notice: Subject to any disclaimer, the term of this patent is extended or adjusted under 35 U.S.C. 154(b) by 842 days.

(21) Appl. No.: 16/073,110

(22) PCT Filed: Apr. 27, 2017

(86) PCT No.: PCT/KR2017/004514
§ 371 (c)(1),
(2) Date: Jul. 26, 2018

(87) PCT Pub. No.: WO2017/188762
PCT Pub. Date: Nov. 2, 2017

(65) Prior Publication Data
US 2019/0041373 A1  Feb. 7, 2019

(30) Foreign Application Priority Data

Apr. 27, 2016 (KR) .................. 10-2016-0051525
Apr. 25, 2017 (KR) .................. 10-2017-0053237

(51) Int. Cl.
*G01N 33/00* (2006.01)
*B64C 39/02* (2006.01)
*G01W 1/10* (2006.01)

(52) U.S. Cl.
CPC ....... *G01N 33/0062* (2013.01); *B64C 39/024* (2013.01); *G01N 33/0073* (2013.01);
(Continued)

(58) Field of Classification Search
CPC .......... G01N 33/0062; G01N 33/0073; G01N 21/94; G01N 2021/945; G01N 21/88;
(Continued)

(56) References Cited

U.S. PATENT DOCUMENTS 3,645,694 A     2/1972  Flatau
4,725,733 A *   2/1988  Horman ................ G01J 5/0014
                                                      250/330
(Continued)

FOREIGN PATENT DOCUMENTS

JP    2013-242276 A    12/2013
JP    2016-064768 A    4/2016
(Continued)

OTHER PUBLICATIONS

International Search Report (PCT/ISA/210) dated Jul. 21, 2017 issued by the International Searching Authority in counterpart International Application No. PCT/KR2017/004514.
(Continued)

*Primary Examiner* — Yoshihisa Ishizuka
(74) *Attorney, Agent, or Firm* — Sughrue Mion, PLLC

(57) ABSTRACT

Provided is a contamination detecting system including at least one moving device; a monitoring unit configured to detect whether a contamination situation is occurring; a control unit configured to dispatch the at least one moving device in an anticipated contaminated region in response to the occurrence of a contamination situation, configure a moving route of the moving device, and controlling a contamination detecting operation of the moving device; a map receiving unit configured to receive an anticipated
(Continued)

contamination map for the anticipated contamination region from the moving device; and a map updating unit configured to receive a contamination detection result of the moving device in a region corresponding to the anticipated contamination map and updates the anticipated contamination map in correspondence thereto.

15 Claims, 18 Drawing Sheets

(52) U.S. Cl.
CPC ......... *G01W 1/10* (2013.01); *B64C 2201/123* (2013.01); *B64C 2201/127* (2013.01); *G01N 2033/0068* (2013.01)

(58) Field of Classification Search
CPC ........ G01N 33/0068; G01N 2033/0068; B64C 39/024; B64C 2201/123; B64C 2201/12; B64C 2201/127; G01W 1/10
See application file for complete search history.

(56) References Cited

U.S. PATENT DOCUMENTS

| | | | |
|---|---|---|---|
| 7,073,748 | B2 | 7/2006 | Maurer et al. |
| 8,409,524 | B2 | 4/2013 | Farmer et al. |
| 2005/0230527 | A1 | 10/2005 | Silansky et al. |
| 2007/0030173 | A1* | 2/2007 | Goossen ................. G01W 1/10 340/971 |
| 2008/0195329 | A1* | 8/2008 | Prince ................ G01N 33/0027 702/23 |
| 2010/0094565 | A1* | 4/2010 | Prince ..................... G01N 1/26 702/22 |
| 2010/0265329 | A1* | 10/2010 | Doneker .......... H04N 5/232933 348/144 |
| 2015/0334768 | A1* | 11/2015 | Ranasinghe .......... H04W 4/023 370/328 |
| 2016/0070265 | A1* | 3/2016 | Liu ........................ G01C 21/00 701/3 |
| 2016/0214715 | A1* | 7/2016 | Meffert ................... G01W 1/00 |
| 2016/0364989 | A1* | 12/2016 | Speasl .................. G08G 5/0034 |

FOREIGN PATENT DOCUMENTS

| | | |
|---|---|---|
| KR | 10-2010-0106092 A | 10/2010 |
| KR | 10-1009456 B1 | 1/2011 |
| KR | 10-1103846 B1 | 1/2012 |
| KR | 10-2012-0071816 A | 7/2012 |
| KR | 10-2014-0123835 A | 10/2014 |
| KR | 10-2015-0069571 A | 6/2015 |
| KR | 10-1530646 B1 | 6/2015 |
| KR | 10-2017-0122492 A | 11/2017 |
| WO | 2014/207492 A1 | 12/2014 |

OTHER PUBLICATIONS

Written Opinion (PCT/ISA/237) dated Jul. 21, 2017 issued by the International Searching Authority in counterpart International Application No. PCT/KR2017/004514.
Communication dated Apr. 27, 2020, issued by the Korean Intellectual Property Office in corresponding Korean Application No. 10-2016-0051525.

* cited by examiner

MOVING DEVICE FOR CONTAMINATION DETECTION, CONTAMINATION DETECTING SYSTEM AND METHOD, AND COMPUTER-READABLE RECORDING MEDIUM

This is a National stage of Application No. PCT/KR2017/004514 filed Apr. 27, 2017, claiming priority based on Korean Patent Application Nos. 10-2016-0051525 filed on Apr. 27, 2016 and 10-2017-0053237 filed on Apr. 25, 2017, the contents of all of which are incorporated herein by reference in their entirety.

TECHNICAL FIELD

The present invention relates to a moving device for detecting contamination, a contamination detecting system, a contamination detecting method, and a computer-readable recording medium, and more particularly, to a moving device capable of detecting a chemical substance, and a contamination detecting system, a contamination detecting method, and a computer-readable recording medium for performing contamination detections by using the moving device, generating a contamination map based on results of the contamination detections, and continuously updating the contamination map, thereby preventing human from being exposed to contaminants.

BACKGROUND ART

Conventional chemical detecting systems requires a man to enter a hazardous region and check a chemical hazard situation when a chemical hazard situation occurs. However, in a region like as a demilitarized zone where mines are buried, people entering into the hazardous region will highly likely cause life damage.

Also, when a person moves in a hazardous region, maneuverability is deteriorated.

Therefore, it is necessary to develop a technique that can quickly perform a contamination detecting operation and minimize life damage.

DESCRIPTION OF EMBODIMENTS

Technical Problem

The present invention provides a moving device for detecting a contamination, a contamination detecting system, a contamination detecting method, and a computer-readable recording medium, capable of preventing human from being exposed to contaminants.

Solution to Problem

According to an aspect of the present invention, there is provided a moving device for detecting contamination including main body; at least one flight device installed in the main body; a detecting unit installed in the main body and capable of exposing a detection sheet for detecting a chemical substance to the outside during detection; and an image capturing unit mounted on the main body and configured to capture an image of the detection sheet exposed to the outside, wherein the detection unit includes a sheet frame supporting shaft; a sheet frame unit rotatably mounted on the sheet frame supporting shaft and provided with the detection sheet; a cam gear unit configured to rotate the sheet frame unit; a rotating shaft on which the cam gear unit is mounted; and a drive motor configured to provide power to the rotating shaft.

Furthermore, a rotating gear is installed on one side of the sheet frame unit, and teeth of the cam gear unit may engage with the rotating gear.

Also, the sheet frame unit includes a plurality of sheet frames, the cam gear unit includes a plurality of cam gears, and the plurality of cam gears may be installed at pre-set angles along the rotating direction of the rotating shaft.

Furthermore, the detecting unit may include a chamber unit having a plurality of chambers, and the sheet frame and the cam gear may be arranged in each of the chambers.

Furthermore, the chamber may be provided with a sealing door, and the sealing door may be provided with a hinge structure.

Furthermore, the main body is provided with a communication device configured to transmit an image of a detection sheet captured by the image capturing unit.

According to another aspect of the present invention, there is provided a contamination detecting system including at least one moving device; a monitoring unit configured to detect whether a contamination situation is occurring; a control unit configured to dispatch the at least one moving device in an anticipated contaminated region in response to the occurrence of a contamination situation, configure a moving route of the moving device, and controlling a contamination detecting operation of the moving device; a map receiving unit configured to receive an anticipated contamination map for the anticipated contamination region from the moving device; and a map updating unit configured to receive a contamination detection result of the moving device in a region corresponding to the anticipated contamination map and updates the anticipated contamination map in correspondence thereto.

The contamination detecting system further includes a weather information providing unit for providing weather information to the moving device, wherein the moving device includes a map generating module configured to generate the anticipated contamination map by using a wind direction and a wind speed measured in the anticipated contaminated region and the weather information.

Furthermore, the controller configures a moving route of the moving device by taking a wind direction in the anticipated contamination region into account for the moving device to move along the wind direction and controls a contamination detecting operation of the moving device on the moving route.

Furthermore, the control unit configures a contamination detecting location of the moving device by taking a wind direction on the moving route of the moving device into account.

Furthermore, the control unit configures the moving route of the moving device by taking a contamination map updated by the map updating unit into account, and the moving route is configured as a closed loop route including a reference location.

Furthermore, the control unit dispatches a plurality of moving devices in the anticipated contamination region and configures a moving route for each of the plurality of moving devices by taking a movable distance of each of the plurality of moving devices or a task assigned to each of the plurality of moving devices into account.

Furthermore, the moving device includes a communication module configured to transmit a result of the contamination detection; a detecting module configured to expose a detection sheet for detecting a contamination to the outside;

and an image capturing module, wherein the result of the contamination detection includes an image of the detection sheet obtained by using the image capturing module.

Furthermore, the moving device captures an image of a projectile dropped in the anticipated contamination region, recognizes a type and a size of the projectile, and transmits recognized information to the map updating unit.

According to another aspect of the present invention, there is provided a method of contamination detection using at least one moving device, the method including detecting whether a contamination situation is occurring; dispatching the moving device in an anticipated contamination region in response to the occurrence of the contamination situation; generating, by the moving device, an anticipated contamination map for the anticipated contamination region; receiving the anticipated contamination map from the moving device, configuring a moving route of the moving device in correspondence to the anticipated contamination map, and configuring an operation of the moving device including a contamination detection location; and receiving a contamination detection result from the moving device and updating the anticipated contamination map in correspondence to the contamination detection result.

Furthermore, the method further includes providing weather information to the moving device, wherein, in the generating of the anticipated contamination map, the anticipated contamination map is generated by the moving device using a wind direction and a wind speed measured by the moving device in the anticipated contamination region and the weather information.

Furthermore, in the configuring of the operation of the moving device, a moving route of the moving device is configured by taking a wind direction in the anticipated contamination region into account for the moving device to move along the wind direction and a contamination detecting operation of the moving device on the moving route are configured.

Furthermore, in the configuring of the operation of the moving device, contamination detecting locations of the moving device are configured by taking the wind direction on the moving route of the moving device into account.

Furthermore, the method further includes updating the moving route of the moving device by taking an updated anticipated contamination map into account, wherein the moving route is configured as a closed loop route including a reference location.

Furthermore, In the dispatching of the moving device, a plurality of moving devices are dispatched in the anticipated contamination region, and, in the configuring of the operation of the moving device, a moving route for each of the plurality of moving devices is configured by taking a movable distance of each of the plurality of moving devices or a task assigned to each of the plurality of moving devices into account.

Furthermore, the contamination detection result comprises an image of the detection sheet provided on the moving device, the image taken by the moving device using an imaging capturing module.

Furthermore, the method may further include an operation for capturing an image of a projectile dropped in the anticipated contamination region, recognizing a type and a size of the projectile, and transmitting the recognized information.

According to another aspect of the present invention, there is provided a computer-readable recording medium on which a program for performing the contamination detecting method is recorded.

Other aspects, features, and advantages will become apparent from the following drawings, claims, and detailed description of the invention.

Advantageous Effects of Disclosure

The present invention provides a moving device for detecting a contamination, a contamination detecting system, a contamination detecting method, and a computer-readable recording medium, capable of preventing human from being exposed to contaminants.

BEST MODE

Figure 1:
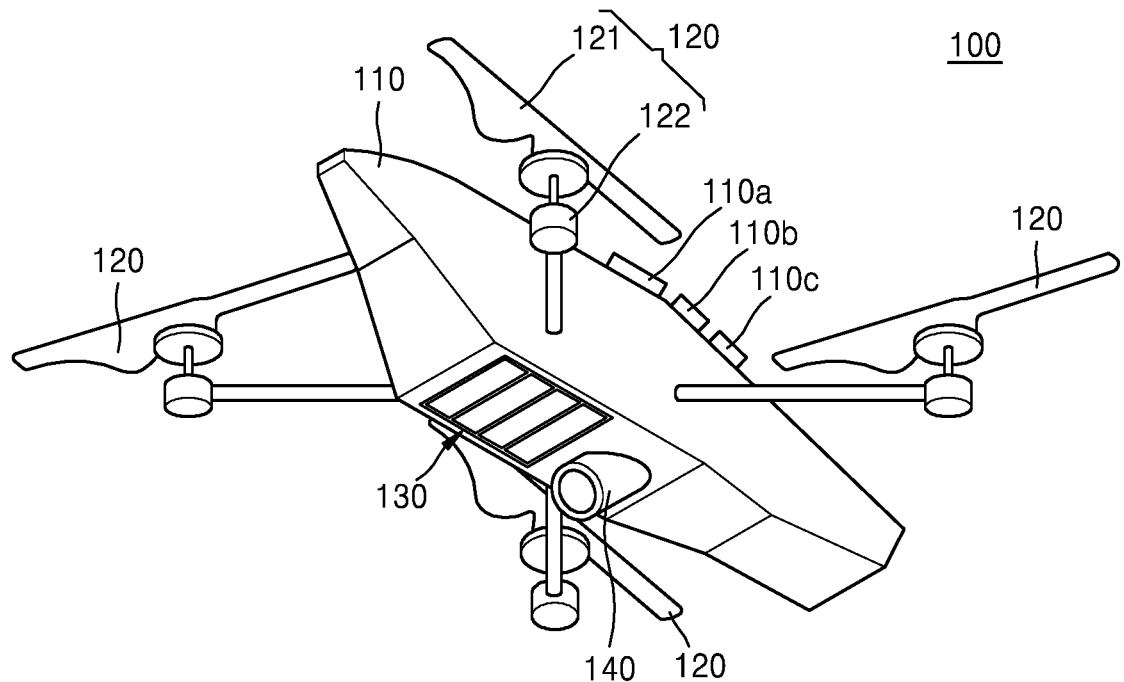
FIG. 1 is a schematic perspective view of a moving device for detecting a contamination according to an embodiment of the present invention.

The present disclosure may include various embodiments and modifications, and embodiments thereof will be illustrated in the drawings and will be described herein in detail.

However, this is not intended to limit the present invention to particular modes of practice, and it is to be appreciated that all changes, equivalents, and substitutes that do not depart from the spirit and technical scope of the present invention are encompassed in the present invention. In the following description of the present disclosure, the detailed description of known functions and configurations incorporated herein is omitted when it may make the subject matter of the present invention rather unclear.

While such terms as "first," "second," etc., may be used to describe various elements, such elements must not be limited to the above terms. The above terms may be used only to distinguish one element from another.

The terms used in the present specification are merely used to describe particular embodiments, and are not intended to limit the present invention. As used herein, the singular forms "a", "an", and "the" are intended to include the plural forms as well, unless the context clearly indicates otherwise. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

The present invention may be described in terms of functional block components and various processing steps. Such functional blocks may be realized by any number of hardware and/or software components configured to perform the specified functions For example, the present invention may employ various integrated circuit (IC) components, e.g., memory elements, processing elements, logic elements, look-up tables, and the like, which may carry out a variety of functions under the control of one or more microprocessors or other control devices. Similarly, where the elements of the present invention are implemented using software programming or software elements, the invention may be implemented with any programming or scripting language such as C, C++, Java, assembler, or the like, with the various algorithms being implemented with any combination of data structures, objects, processes, routines or other programming elements. Functional aspects may be implemented in algorithms that are executed on one or more processors. Furthermore, the present invention could employ any number of conventional techniques for electronics configuration, signal processing and/or control, data processing and the like. The words "mechanism", "element", "means", and "configuration" are used broadly and are not limited to mechanical or physical embodiments, but can include software routines in conjunction with processors, etc.

In the present specification and drawings, the same reference numerals are used for constituent elements having substantially the same configuration, and redundant description is omitted.

As shown in FIGS. 1 to 6, a moving device 100 for detecting contamination includes a main body 110, flight devices 120, a detecting unit 130, and an image capturing unit 140.

The main body 110 is a unit in which a power source 110a like a battery, a communication device 110b, a main control device 110c, and other components of the moving device 100 for detecting contamination are installed, wherein the main body 110 includes a frame, a cover, etc. Here, the main control device 110c includes an electronic circuit, an integrated circuit chip, and the like, and controls the respective components of the moving device 100 for detecting contamination.

The flight devices 120 are devices that enable movement of the moving device 100 for detecting contamination, where four flight devices 120 are rotatably installed to the main body 110 symmetrically.

Each of the flight devices 120 includes a rotor blade 121 and a rotor driving device 122 that rotates and drives the rotor blade 121.

The rotor driving device 122 is installed in the main body 110, and a motor is used as the rotor driving device 122, where various types of motors like a step motor, a servo motor, a general direct current motor, and an alternating current motor may be applied.

Although the rotor blade 121 and the rotor driving device 122 are used for the flight device 120 according to the present embodiment, the present invention is not limited thereto. That is, as a flight device for the present invention, a flight device having various propulsion devices such as a fluid propulsion device and a jet propulsion device may be used instead of a flight device using a rotor blade.

According to the present embodiment, four flight devices 120 are installed symmetrically in the main body 110, but present invention is not limited thereto. In other words, the number of flight devices according to present invention may be at least one, and there is no other particular limitation. For example, the number of flight devices according to present invention may be 1, 2, 3, 5, 6, etc.

On the other hand, the detecting unit 130 may be installed in the main body 110 to expose a detection sheet S for detecting a chemical substance to the outside during detection.

As shown in FIGS. 4 to 8, the detecting unit 130 includes a sheet frame supporting shaft 131, a sheet frame unit 132, a cam gear unit 133, a rotation shaft 134, a driving motor 135, and a chamber unit 136.

The sheet frame unit 132 is installed on the sheet frame supporting shaft 131, such that the sheet frame unit 132 may rotate around the sheet frame supporting shaft 131.

Although the sheet frame supporting shaft 131 according to the present embodiment is continuously installed throughout the entire chamber unit 136, the present invention is not limited thereto. The sheet frame supporting shaft 131 according to the present invention may be installed separately for each of chambers 136a, 136b, 136c, and 136d of the chamber unit 136.

The detection sheet S is installed to the sheet frame unit 132, wherein the sheet frame unit 132 includes four sheet frames 132a, 132b, 132c, and 132d.

Although the sheet frame unit 132 according to the present embodiment includes the four sheet frames 132a, 132b, 132c, and 132d, the present invention is not limited thereto. In other words, there is no particular limitation on the number of sheet frames included in a sheet frame unit according to the present invention. For example, the number of sheet frames included in a sheet frame according to the present invention may be 1, 2, 3, 5, 6, and so on.

The detection sheet S according to the present embodiment includes first, second, third, and fourth detection sheets S1, S2, S3, and S4. The first, second, third, and fourth detection sheets S1, S2, S3 and S4 are installed to the sheet frames 132a, 132b, 132c, and 132d, respectively.

Figure 5:
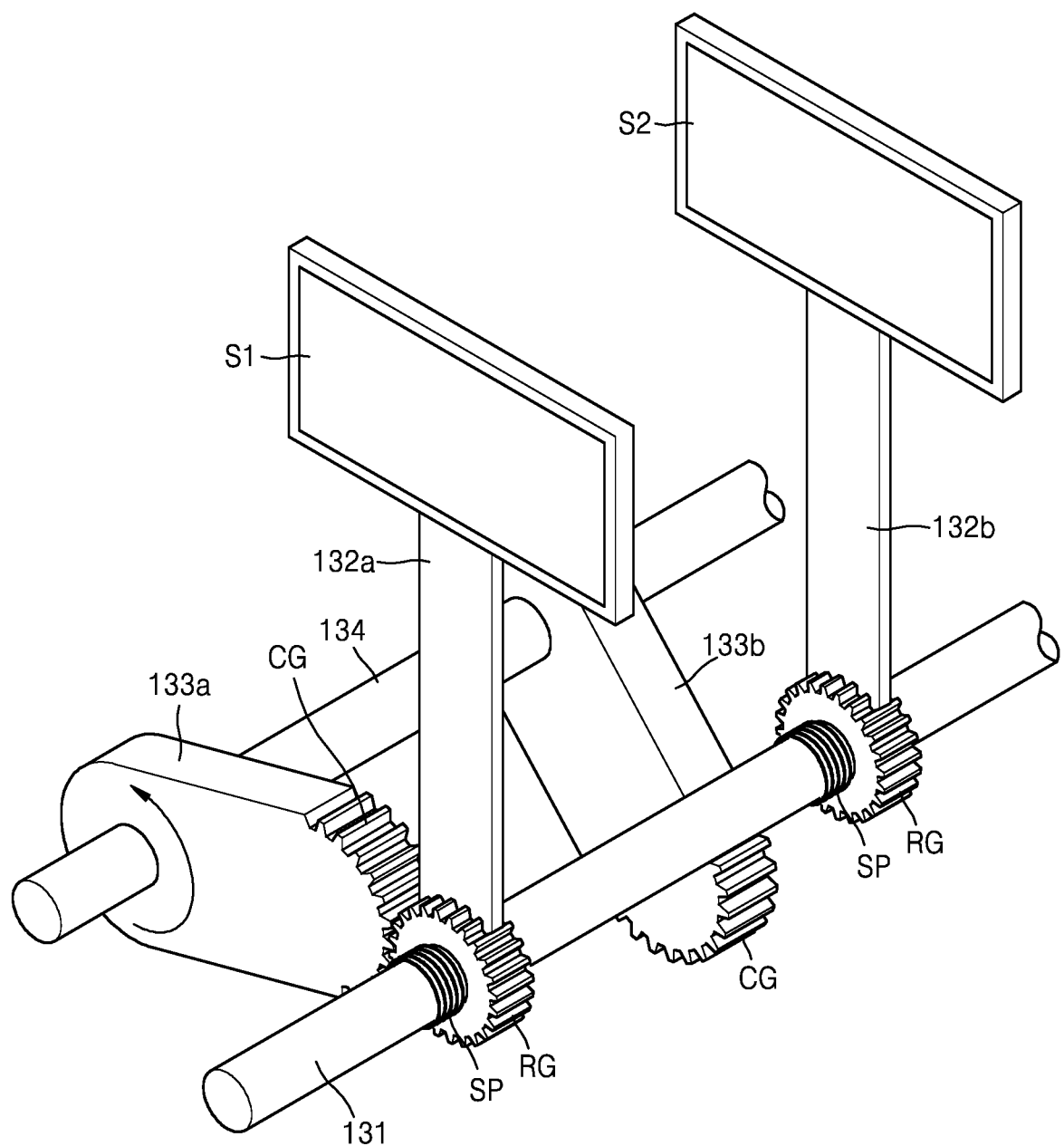
FIG. 5 is a schematic view showing a detection sheet, a sheet frame supporting shaft, a sheet frame unit, a cam gear unit, and a portion of a rotation shaft of a detecting unit of a moving device for detecting contamination according to an embodiment of the present invention.

As shown in FIG. 5, each of the sheet frames 132a, 132b, 132c, and 132d is mounted on the sheet frame supporting shaft 131 using an elastic member SP. Therefore, the sheet frame 132a, 132b, 132c, and 132d stays toward one direction as shown in FIG. 5 due to a elastic restoring force of the elastic member SP unless an external force is applied thereto. Here, the elastic member SP is a cylindrical coil spring. However, the present invention is not limited thereto, and other types of springs may be applied.

In addition, a rotating gear RG is installed at one side of each of the sheet frame 132a, 132b, 132c, and 132d. The rotating gear RG is engaged with gear teeth CG of the cam gear unit 133 and rotate each of the sheet frames 132a, 132b, 132c, and 132d.

Figure 7:
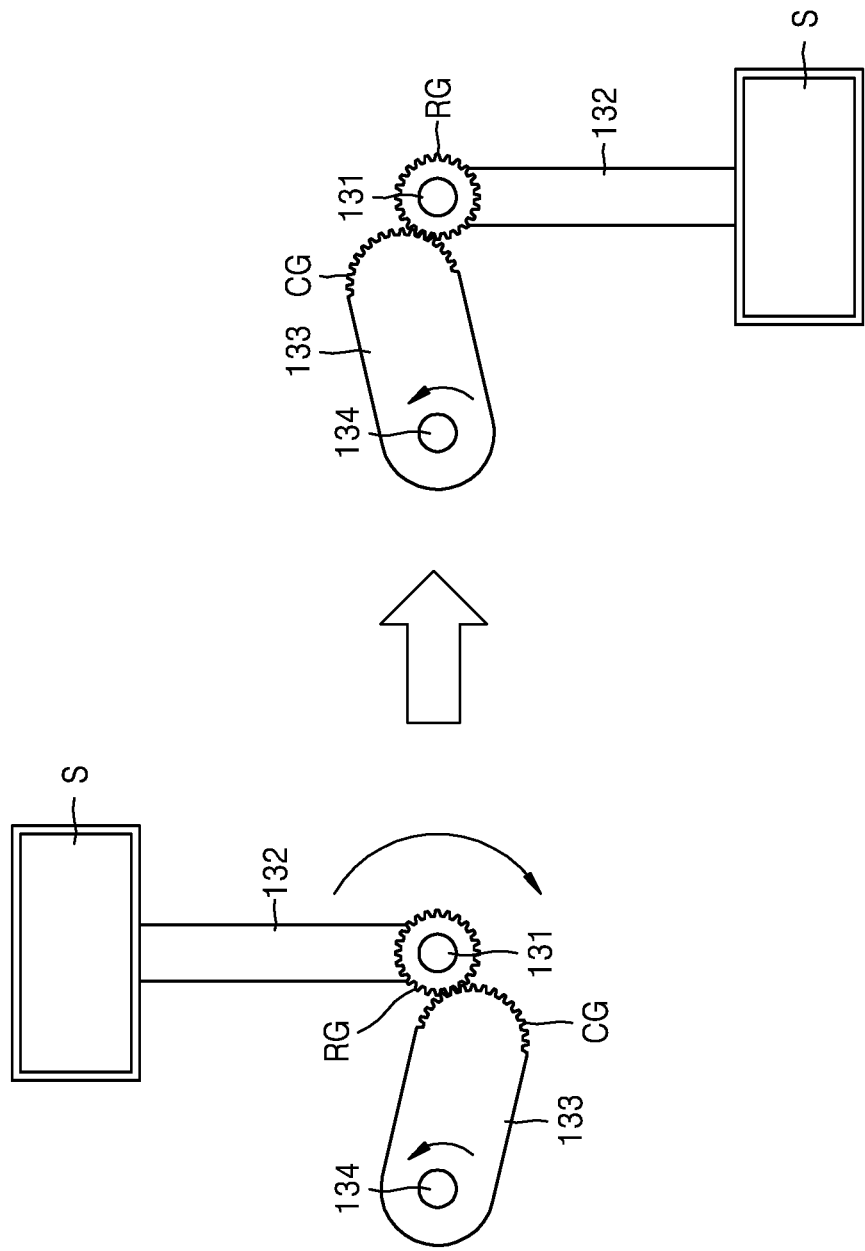
FIG. 7 is a schematic view showing a state in which a sheet frame is rotated by rotation of a cam gear of a detecting unit of a moving device for detecting a contamination according to an embodiment of the present invention.
Figure 8:
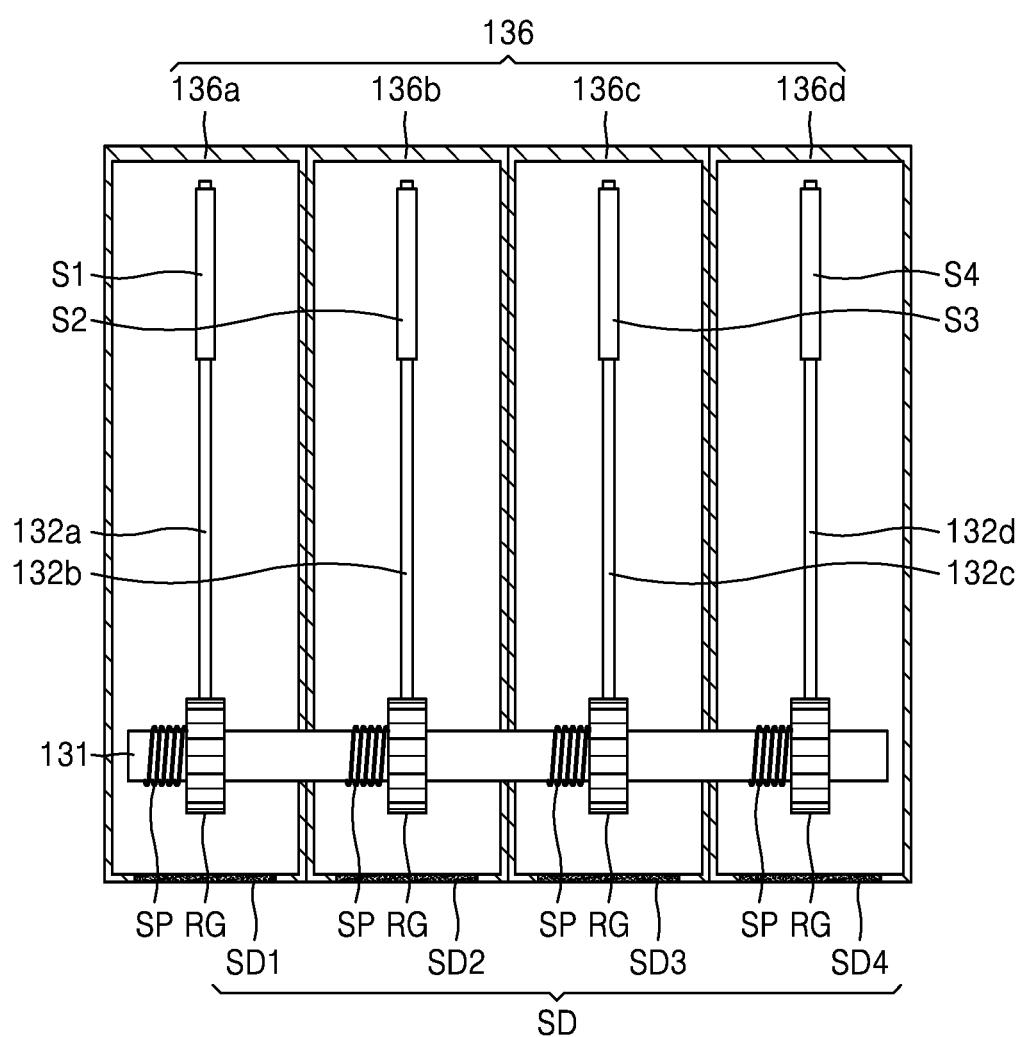
FIG. 8 is a schematic view showing a state in which a detection sheet and a seat frame are installed in each of a plurality of chambers of a moving device for detecting a contamination according to an embodiment of the present invention.

Meanwhile, the cam gear unit 133 rotates the sheet frame unit 132 by engaging with the rotating gear RG of the sheet frame unit 132, as shown in FIG. 7.

Figure 6:
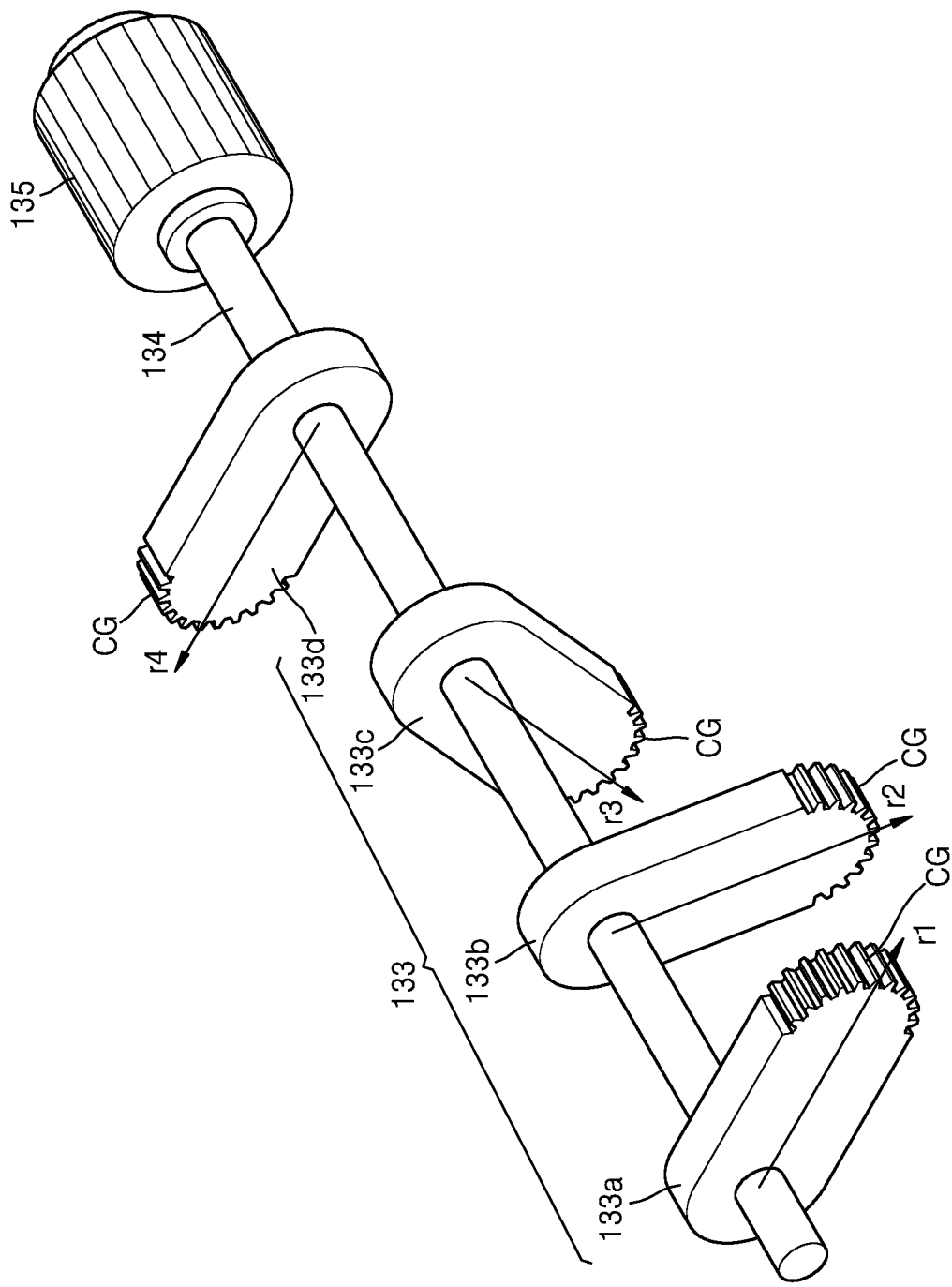
FIG. 6 is a schematic view of a cam gear unit, a rotating shaft, and a driving motor of a detecting unit of a moving device for detecting contamination according to an embodiment of the present invention.

The cam gear unit 133 includes four cam gears 133a, 133b, 133c, and 133d, as shown in FIG. 6. The cam gears 133a, 133b, 133c, and 133d are provided on the rotation shaft 134 at a pre-set interval, wherein the gear teeth CG are formed on one side of each of the cam gears 133a, 133b, 133c, and 133d.

The cam gear unit 133 according to the present embodiment includes four cam gears 133a, 133b, 133c, and 133d, but the present invention is not limited thereto. In other words, there is no particular limitation on the number of cam gears included in a cam gear unit according to the present invention. For example, the number of cam gears included in a cam gear unit according to the present invention may be 1, 2, 3, 5, 6, and so on.

Respective installation directions r1, r2, r3, and r4 of the cam gears 133a, 133b, 133c and 133d are different from one another by certain angles in the direction of rotation of the rotation shaft 134. In this installation configuration, the rotation gears RG of the sheet frames 132a, 132b, 132c, and 132d and the gear teeth CG of the cam gears 133a, 133b, 133c, and 133d are sequentially engaged with each other, thereby sequentially rotating the sheet frames 132a, 132b, 132c, and 132d.

The cam gear unit 133 is installed on the rotation shaft 134, which receives power from the driving motor 135 and rotates the cam gear unit 133.

The driving motor 135 is controlled by the main control device 110c and supplies power to the rotation shaft 134, wherein the driving motor 135 includes a geared motor.

The driving motor 135 according to the present embodiment includes a geared motor, and shaft of the driving motor 135 is directly connected to the rotation shaft 134. However, the present invention is not limited thereto. In other words, according to the present invention, a separate power transmission device, such as a gear and a belt, may be installed between the driving motor 135 and the rotation shaft 134, and the driving motor 135 may not include a geared motor.

Meanwhile, the detecting unit 130 includes the chamber unit 136, which has four chambers 136a, 136b, 136c, and 136d.

The chamber unit 136 according to this embodiment has the four chambers 136a, 136b, 136c, and 136d, but the present invention is not limited thereto. In other words, the number of chambers of the chamber unit according to the present invention is not particularly limited. For example, the number of chambers included in a chamber unit according to the present invention may be 1, 2, 3, 5, 6, and so on.

The sheet frames 132a, 132b, 132c, and 132d and the cam gears 133a, 133b, 133c, and, 133d are disposed in the chambers 136a 136b 136c and 136d, respectively. In addition, a sealing door SD is provided at one side of each of the chambers 136a, 136b, 136c, and 136d with a hinge structure H.

The sealing door SD is configured to include a seal material like rubber. The sealing door SD includes four sealing doors SD1, SD2, SD3, and SD4, and the sealing doors SD1, SD2, SD3, and SD4 are configured to seal the internal spaces of the chambers 136a, 136b, 136c, and 136d.

The hinge structure H for installing the sealing door SD to each of the chambers 136a, 136b, 136c, and 136d includes a hinge pin HP and a hinge spring HS.

The hinge spring HS is installed to give elasticity to the sealing door SD, and thus the sealing door SD is kept closed by hinge Spring HS, except during a detection when the detection sheet S is exposed to the outside. Here, the hinge spring HS is a cylindrical coil spring, but the present invention is not limited thereto, and other types of springs may also be applied.

In other words, except during a detection where the detection sheet S is exposed to the outside, the sealing door SD is kept closed by the hinge spring HS, and thus contamination of the detection sheet S before and after the detection may be prevented.

According to the present embodiment, the sealing door SD is installed with the hinge structure H on one side of the chamber unit 136, but the present invention is not limited thereto. In other words, according to the present invention, there is no particular restriction on the configuration in which a sealing door is installed to a chamber. For example, a sealing door according to the present invention may be installed in a chamber with a sliding structure.

Meanwhile, the image capturing unit 140 is installed in the main body 110, wherein the image capturing unit 140 is installed to capture the detection sheet S exposed to the outside.

The image capturing unit 140 includes an optical system and an imaging device, and various types of cameras capable of capturing still images and moving pictures may be used.

Image data of the detection sheet S captured by the image capturing unit 140 is transmitted through the communication device 110b, and an operation system or an operator receives and analyzes the image data and determine factors including types and concentrations of chemical substance existing in the atmosphere of a detecting region.

However, the present invention is not limited thereto. In other words, according to the present invention, the image data captured by the image capturing unit 140 is transmitted to the main control device 110c, and the main control device 110c may figure out types and concentrations of chemical substances existing in the atmosphere of a detecting region via an image analyzing program embedded in the main control device 110c.

Hereinafter, with reference to the above-mentioned drawings, a mechanism for detecting chemical substances existings in various detecting regions by using the flight moving device 100 according to the present embodiment will be described.

First, the flight moving device 100 moves to a first detecting region according to a pre-input route or a remote control.

After the flight moving device 100 moves to the first detecting region, the main control device 110c drives the driving motor 135.

The driving motor 135 moves the rotation shaft 134 by a pre-set angle. In this case, the four cam gears 133a, 133b, 133c, and 133d provided on the rotation shaft 134 are also rotated by pre-set angles.

When the gear teeth CG of the cam gear 133a of the rotating cam gear unit 133 engages and is rotated with the rotating gear RG of a first sheet frame 132a, the first sheet frame 132a is rotated. At this time, since the gear teeth CG of the remaining cam gears 133b, 133c, and 133d did not contact the rotating gears RG of the sheet frames 132b, 132c, and 132d, the postures of the remaining sheet frames 132b, 132c, and 132d are maintained in the initial state by the member SP.

As the cam gear 133a rotates, the sheet frame 132a also rotates. In this case, as the sheet frame 132a pushes the sealing door SD1, a first detection sheet S1 is gradually exposed to the outside of the chamber 136a.

Figure 2:
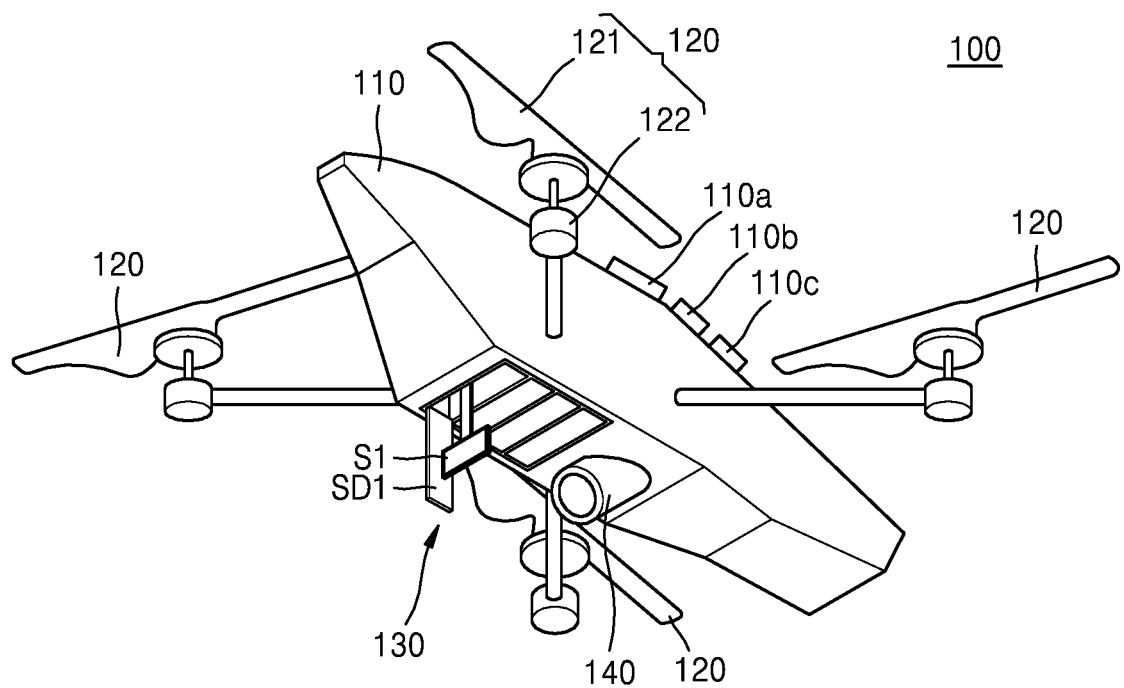
FIG. 2 is a schematic perspective view showing a state in which a first detection sheet is exposed to the outside from a mobile device for detecting contamination according to an embodiment of the present invention.
Figure 9:
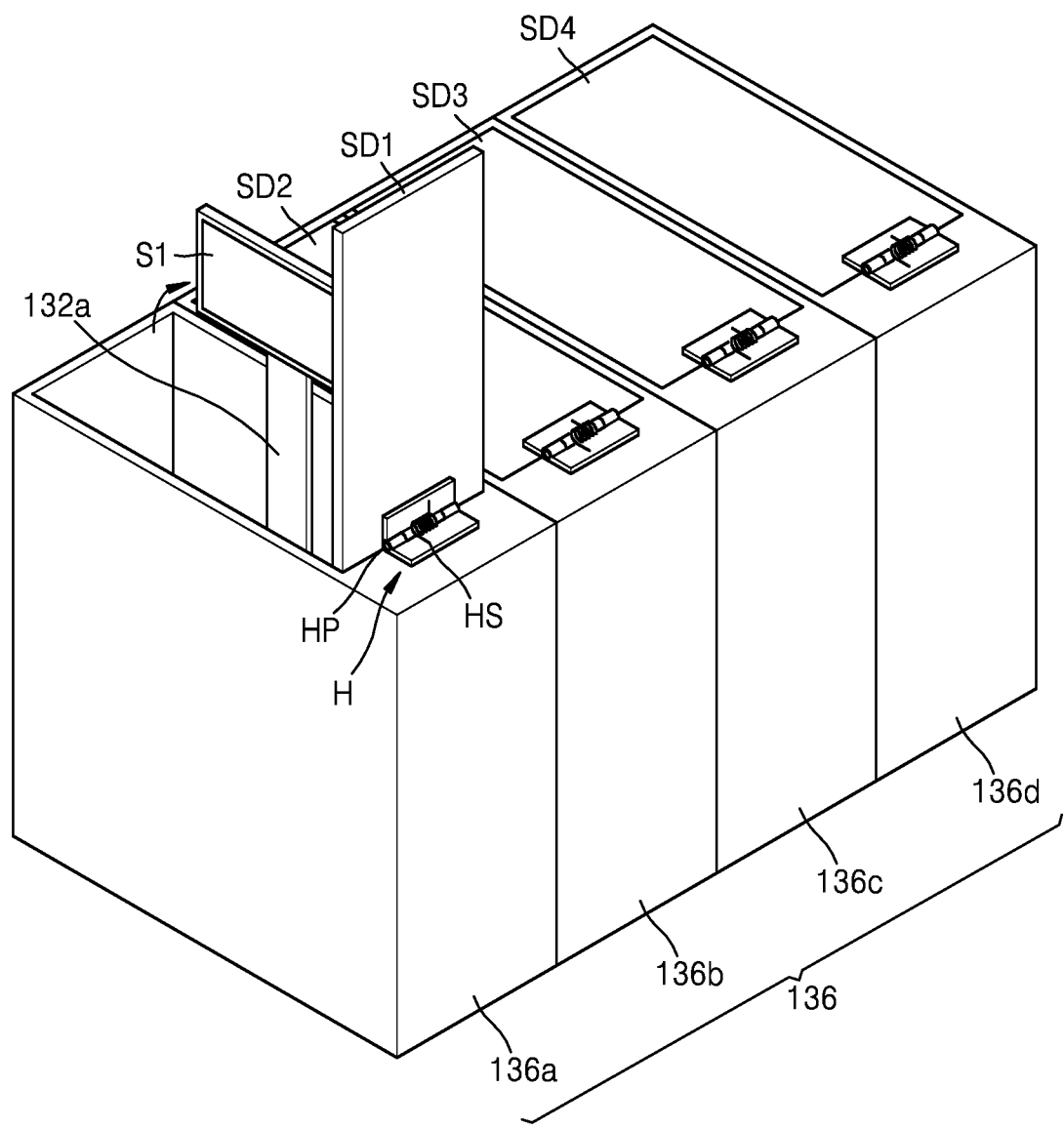
FIG. 9 is a schematic perspective view showing a state in which a first detection sheet is exposed to the outside of a chamber unit of a mobile device for detecting contamination according to an embodiment of the present invention.

As shown in FIGS. 2 and 9, when the first detection sheet S1 is completely exposed to the outside of the chamber 136a and a chemical substance to be detected exists in the atmosphere of the first detecting region, the first detection sheet S1 engages into a chemical reaction with the chemical substance existing in the atmosphere of the first detecting region and changes color.

At this time, the image capturing unit 140 captures image data of the first detection sheet S1 exposed to the outside, and the captured image data is transmitted to an operation system or an operator through the communication device 110b. As a result, the chemical substance is detected.

Next, the main control device 110c drives the driving motor 135 to further move the rotation shaft 134 by a pre-set angle. At this time, the engagement of the gear teeth CG of the cam gear 133a with the rotating gear RG of the first sheet frame 132a is released. As a result, the sheet frame 132a and the first detection sheet S1 exposed to the outside of the chamber 136a are returned to the inside of the chamber 136a by the elastic restoring force of the elastic member SP. At this time, since the sheet frame 132a does not have force pushing the sealing door SD1, the sealing door SD1 is closed by the elastic restoring force of the hinge spring HS.

When a chemical detecting operation for the first detecting region is completed, the moving device 100 for detecting contamination moves a second detecting region according to a pre-input route or a remote control. The main control device 110c of the moving device 100 for detecting contamination that moved to the second detecting region drives the driving motor 135 again.

The driving motor 135 moves the rotation shaft 134 by a pre-set angle. In this case, the four cam gears 133a, 133b, 133c, and 133d provided on the rotation shaft 134 are also rotated by pre-set angles.

When the gear teeth CG of the cam gear 133b of the rotating cam gear unit 133 engages and is rotated with the rotating gear RG of a second sheet frame 132b, the second sheet frame 132b is rotated. At this time, since the gear teeth CG of the remaining cam gears 133a, 133c, and 133d did not contact the rotating gears RG of the sheet frames 132a, 132c, and 132d, the postures of the remaining sheet frames 132a, 132c, and 132d are maintained in the initial state by the member SP.

As the cam gear 133b rotates, the sheet frame 132b also rotates. In this case, as the sheet frame 132b pushes the sealing door SD2, a second detection sheet S2 is gradually exposed to the outside of the chamber 136b.

Figure 3:
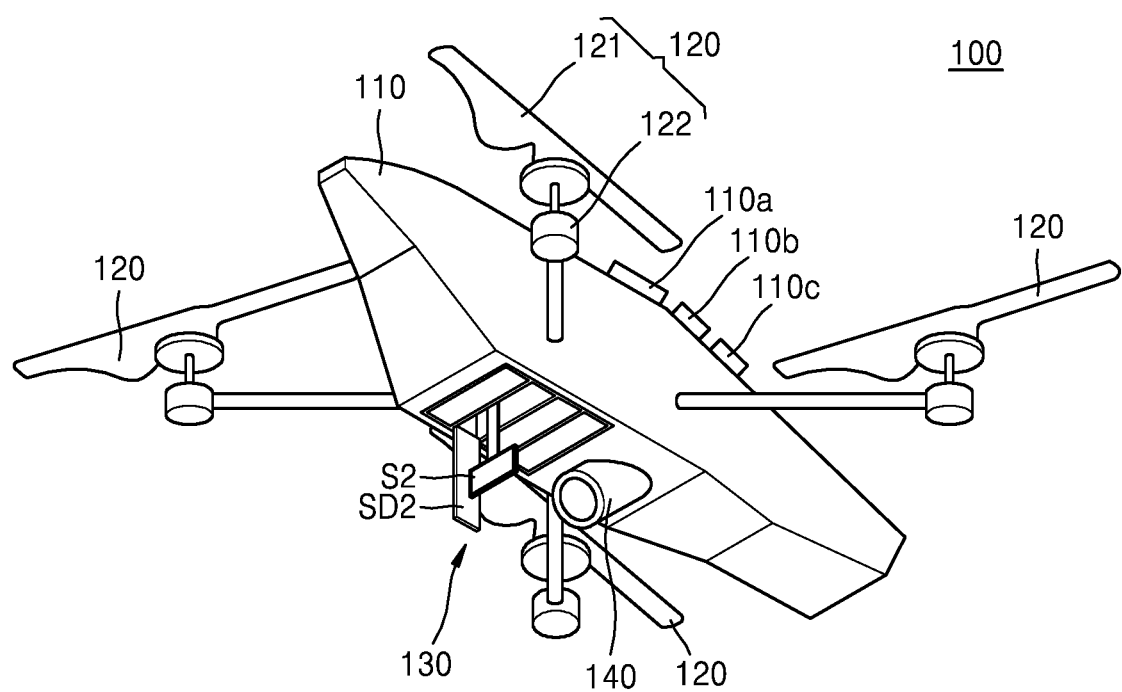
FIG. 3 is a schematic perspective view showing a state in which a second detection sheet is exposed to the outside from a mobile device for detecting contamination according to an embodiment of the present invention.
Figure 4:
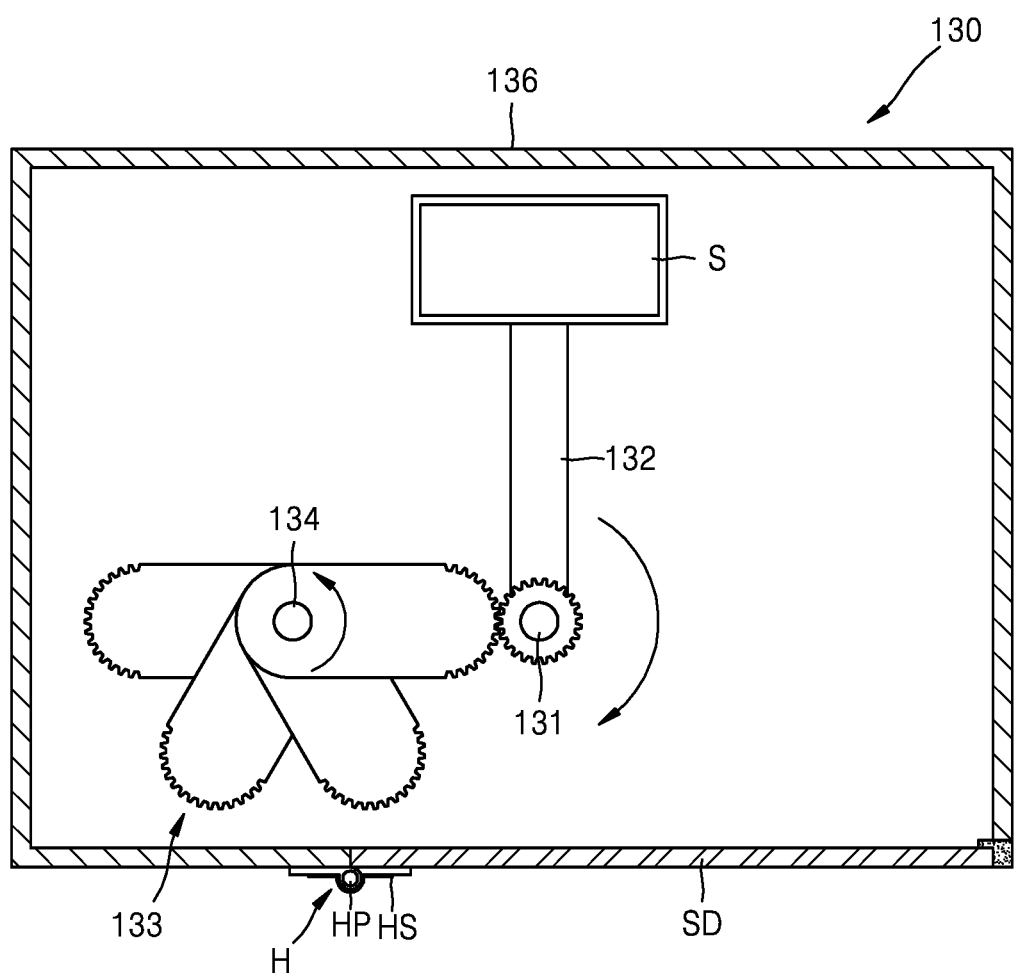
FIG. 4 is a schematic perspective view of an operation of a detecting unit of a moving device for detecting a contamination according to an embodiment of the present invention.

As shown in FIG. 3, when the second detection sheet S2 is completely exposed to the outside of the chamber 136b and a chemical substance to be detected exists in the atmosphere of the second detecting region, the second detection sheet S2 engages into a chemical reaction with the chemical substance existing in the atmosphere of the second detecting region and changes color.

At this time, the image capturing unit 140 captures image data of the second detection sheet S2 exposed to the outside, and the captured image data is transmitted to an operation system or an operator through the communication device 110b. As a result, the chemical substance is detected.

Next, the main control device 110c drives the driving motor 135 to further move the rotation shaft 134 by a pre-set angle. At this time, the engagement of the gear teeth CG of the cam gear 133b with the rotating gear RG of the second sheet frame 132b is released. As a result, the sheet frame 132b and the second detection sheet S2 exposed to the outside of the chamber 136b are returned to the inside of the chamber 136b by the elastic restoring force of the elastic member SP. At this time, since the sheet frame 132b does not have force pushing the sealing door SD2, the sealing door SD2 is closed by the elastic restoring force of the hinge spring HS.

A method of detecting chemical substances in the first detecting region and the second detecting region has been described above. The above method may be repeatedly applied as-is to the detection of chemical substances using third and fourth detection sheets S3 and S4 respectively located at the chambers 136c and 136d. Therefore, detailed description thereof will be omitted.

Meanwhile, a detection reagent is applied to the detection sheet S according to the present embodiment in advance, but the present invention is not limited thereto. In other words, no detection reagent may be applied to a detection sheet according to the present invention in advance. In this case, a detection reagent sprayer (not shown) containing a detection reagent may be installed in the main body 110, and the detection reagent sprayer may be used to apply the detection reagent to a detection sheet before detection of a chemical substance.

As described above, according to the present embodiment, since a chemical substance is detected by moving the moving device 100 for detecting contamination to a chemical detecting region, exposing the detection sheet S to the outside, and capturing an image of the detection sheet S, a chemical substance may be detected accurately and quickly. Moreover, when the moving device 100 for detecting contamination is operated as an unmanned device, possible life damages due to chemical substance contamination may be prevented.

The detecting unit 130 of the moving device 100 for detecting contamination according to the present embodiment may detect a chemical substance accurately and quickly by exposing the detection sheet S during detection of a chemical substance by using the sheet frame supporting shaft 131, the sheet frame unit 132, the cam gear unit 133, the rotation shaft 134, and the driving motor 135.

Furthermore, since the moving device 100 for detecting contamination according to the present embodiment includes the first, second, third, and fourth detection sheets S1, S2, S3, and S4 respectively in the plurality of chambers 136a, 136b, 136c, and 136d, a plurality of detections may be performed through one dispatch. Furthermore, when the operator is planning to detect several types of chemical substances, by appropriately arranging types of detection reagents applied to the detection sheets S1, S2, S3 and S4, several types of chemical substances may be detected.

Although aspects of the present invention are described with reference to the embodiments illustrated in the accompanying drawings, they are merely examples, and one of ordinary skill in the art will understand that various modifications and other equivalent embodiments may be derived therefrom. Accordingly, the true scope of the present invention to be protected should be determined only by the appended claims.

Mode of Disclosure

Figure 10:
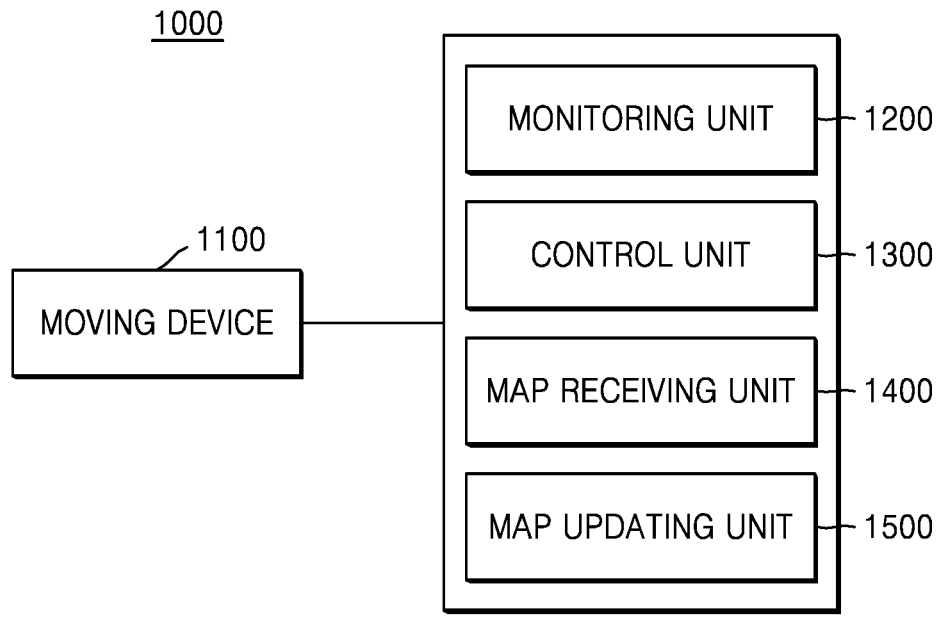
FIG. 10 is a diagram schematically showing a configuration of a contamination detecting system according to an embodiment of the present invention.

FIG. 10 is a diagram schematically showing a configuration of a contamination detecting system according to an embodiment of the present invention.

Referring to FIG. 10, a contamination detecting system 1000 according to an embodiment of the present invention includes a moving device 1100, a monitoring unit 1200, a control unit 1300, a map receiving unit 1400, and a map updating unit 1500.

The moving device 1100 refers to an unmanned device that performs a contamination detecting operation in contamination detecting system and method according to the present invention and may detect a hazardous situation occurring in a region difficult for a human to access. Meanwhile, it may be understood that the moving device 1100 includes a driving unit (not shown) that enables movements on land, in the air, or in the water, and the contamination detecting system and method according to the present invention may detect a contamination by using at least one moving device 1100.

The monitoring unit 1200 detects a contamination situation. A detecting operation performed by the monitoring unit 1200 is an operation not for detecting whether an actual contamination situation is occurred, but for detecting whether a contamination situation is anticipated. For example, the monitoring unit 1200 may monitor whether an object assumed as a chemical projectile is dropped in a certain region or receive an alarm or a notification received from the outside.

The control unit 1300 dispatches the moving device 1100 in an anticipated contaminated region in response to the contamination situation. When the monitoring unit 1200 anticipates that a contamination situation is occurring, the control unit 1300 dispatches at least one moving device 1100 in a region that is anticipated to be contaminated. At this time, the control unit 1300 may set a moving route of the moving device 1100 and control a contamination detecting operation.

The moving route may include a route from a starting point to a destination of the moving device 1100 and a route for returning from the destination to the starting point, wherein the moving route may be changed by the control unit 1300 at any time.

Meanwhile, the control unit 1300 may control a contamination detecting operation of the moving device 1100 on the moving route. The control unit 1300 may control the moving device 1100 to perform an appropriate contamination detecting operation by taking a location and a surrounding environment of the moving device 1100 into account.

For example, when it is anticipated that an initial contamination situation is occurring, the moving device 1100 may be controlled not to perform a contamination detecting operation other than a moving operation while the moving device 1100 is moving from the starting point to the anticipated contamination region. Furthermore, when the moving device 1100 arrives at the anticipated contamination region, the moving device 1100 may be controlled to perform a contamination detecting operation so as to determine whether a contamination is actually occurring at the destination.

The map receiving unit 1400 receives an anticipated contamination map for the anticipated contamination region from the moving device 1100. The anticipated contamination map may include anticipated contamination information about a region in which occurrence of the contamination situation is anticipated and surrounding regions, and the anticipated contamination information may be generated in consideration of a type of a contamination material dropped into the anticipated contamination region and surrounding environments including terrain of the anticipated contamination region.

The map updating unit 1500 receives a contamination detecting result of the moving device 1100 in a region corresponding to the anticipated contamination map and updates the anticipated contamination map in correspondence to the contamination detecting result.

As described above, the control unit 1300 may control a contamination detecting operation of the moving device 1100, wherein the moving device 1100 may perform a contamination detecting operation under the control of the control unit 1300. When the map receiving unit 1400 receives the anticipated contamination map, the control unit 1300 may designate a location for the moving device 1100 to detect a contamination and a contamination detecting operation to be performed at the corresponding location based on the anticipated contamination map.

The moving device 1100 may perform an operation corresponding to a control command of the control unit 1300 and may transmit a result of performing the operation to the map updating unit 1500. The map updating unit 1500 may generate a corrected contamination map by comparing information included in the anticipated contamination map with a result of a contamination detecting operation transmitted from the moving device 1100 and updating the anticipated contamination map. The corrected contamination map may provide information for performing an effective and safe decontaminating operation for a contamination region.

Figure 11:
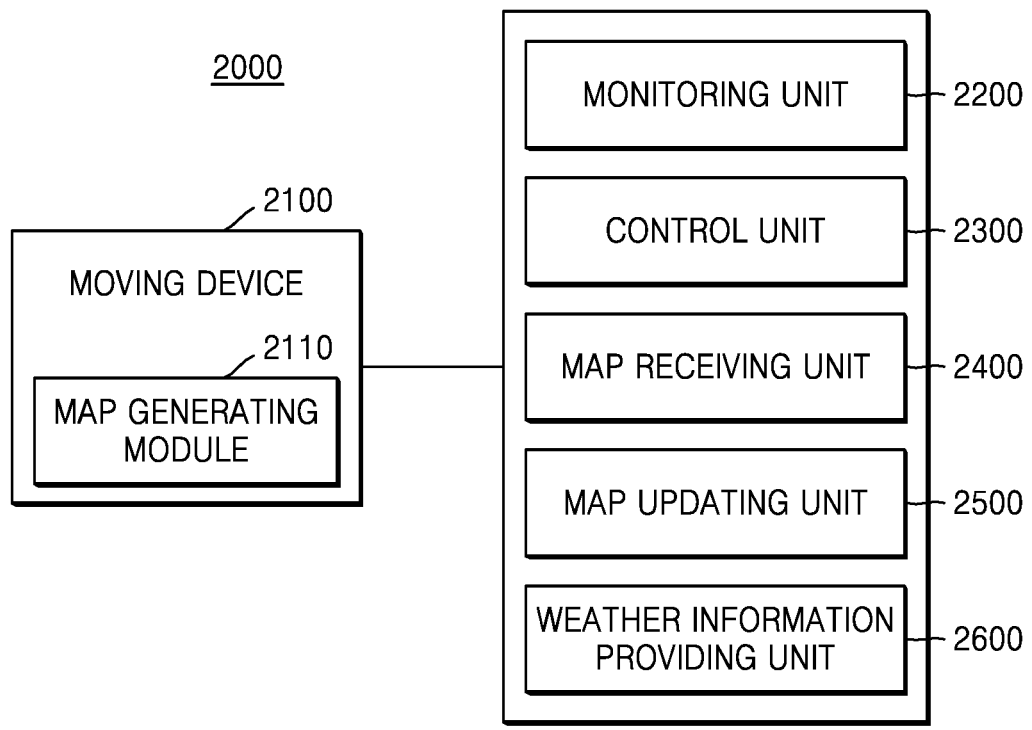
FIG. 11 is a schematic view of a configuration of a contamination detecting system according to another embodiment of the present invention.

FIG. 11 is a schematic view of a configuration of a contamination detecting system according to another embodiment of the present invention.

Referring to FIG. 11, a contamination detecting system 2000 according to another embodiment of the present invention further includes a moving device 2100, which includes a map generating module 2110, and a weather information providing unit 2600.

The weather information providing unit 2600 provides weather information of an anticipated contamination region to the moving device 2100, and the map generating module 2110 generates an anticipated contamination map by using a wind direction and a wind speed measured in the anticipated contamination region and the weather information.

The weather information provided by the weather information providing unit 2600 may include information like the temperature, the humidity, and the precipitation of the anticipated contamination region, and the map generating module 2110 may analyze information directly measured by the moving device 2100 in the anticipated contamination region, such as a wind direction and a wind speed, and the weather information and calculate a direction, a range, and/or a speed at which contaminants in the anticipated contamination region are anticipated to spread.

Figure 12:
FIGS. 12 and 13 are diagrams showing examples of an anticipated contamination map according to embodiments of the present invention.
Figure 13:
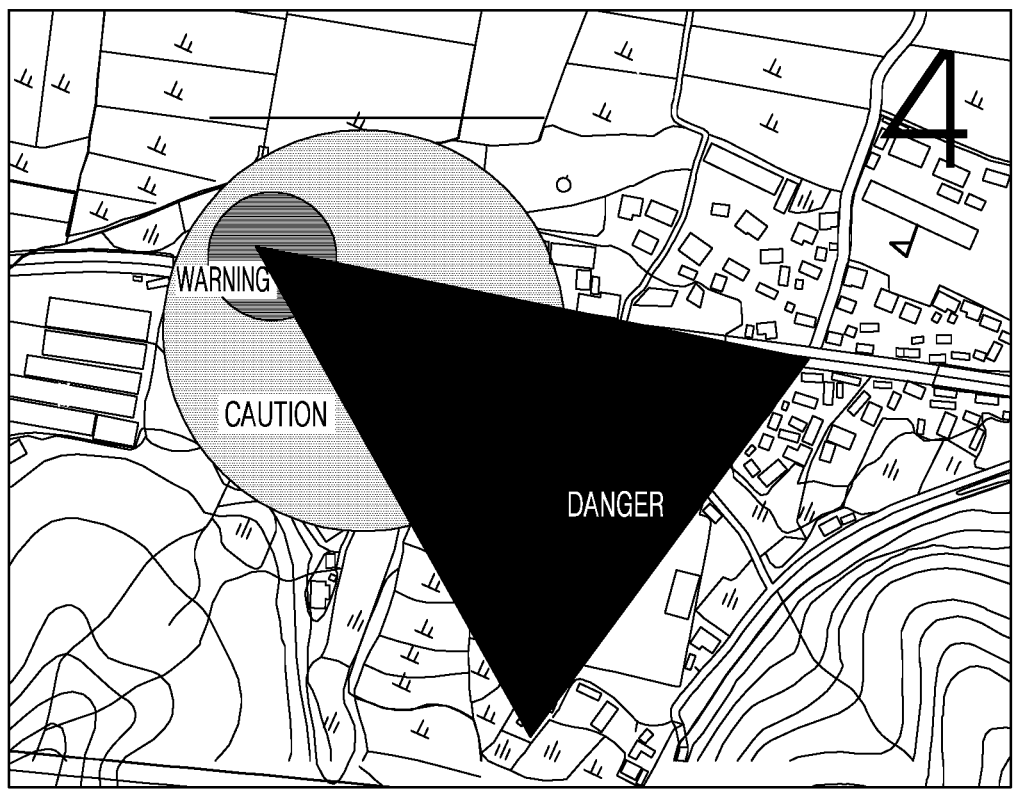

FIGS. 12 and 13 are diagrams showing examples of an anticipated contamination map according to embodiments of the present invention.

First, referring to FIG. 12, a location H indicates an initial starting point of the moving device 2100, and a location Z is a location included in an anticipated contamination region and indicates a destination of the moving device 2100 set by the control unit 2300.

The moving device 2100 may arrive at the location Z, perform a contamination detection, and determine whether the anticipated contamination region is actually contaminated based on a result of the contamination detection. When it is determined that the anticipated contamination region is actually contaminated, an anticipated contamination map may be generated by using a wind direction and a wind speed measured at the location Z and weather information provided by the weather information providing unit 2600.

FIG. 12 exemplifies an anticipated contamination map generated when a northwest wind blows, and the location Z may be understood as a location at which a contaminant was initially dropped.

FIG. 13 exemplifies an anticipated contamination map according to another embodiment of the present invention. Referring to FIG. 13, warning, caution, and danger regions are distinctively displayed on the anticipated contamination map shown in FIG. 13. A warning region refers to a location at which a contaminant was initially dropped and a region surrounding the location, and a caution region may refer to a region that needs attention although the risk of the contaminant spreading thereto is low. Furthermore, a danger region may refer to a region where the contaminant is anticipated to spread in the future and corresponds to the anticipated contamination map described above with reference to FIG. 12.

The warning, caution, and danger regions may be referred to as other terms as needed, and the location and the size of each region may vary as needed.

Figure 14:
FIG. 14 is a diagram exemplifying a moving route of a moving device in an anticipated contamination region.

FIG. 14 is a diagram exemplifying a moving route of a moving device in an anticipated contamination region.

The anticipated contamination maps described above with reference to FIGS. 12 and 13 are maps showing contamination information anticipated based on a location where a contaminant was initially dropped and various weather information and may not reflect an actual contamination situation. Therefore, a process for accurately determining whether a contamination situation is occurring at a location corresponding to the anticipated contamination map and the degree of the contamination is necessary.

In order to accurately determine a contamination situation, the control unit 2300 may newly set a moving route of the moving device 2100 by taking the anticipated contamination map into an account and control a contamination detecting operation of the moving device 2100 on the moving route.

In FIG. 14, locations 1 to 4 exemplify some locations on a moving path of the moving device 2100, and it may be understood that the moving device 2100 sequentially moves from a location 1 to a location 4. The moving route may be set by taking the anticipated contamination map and a wind direction in the anticipated contamination region into account. Since a northwest wind is detected at a location Z of the anticipated contamination region, which is the initial arrival point of the moving device 2100, the control unit 2300 may set a moving route of the moving device 2100 from the location Z to the location 1.

It may be understood that the moving route is set to be nearby edges of the anticipated contamination map in order to more accurately determine whether a region corresponding to a boundary of the anticipated contamination map is contaminated.

Furthermore, at the location 1, a new moving route may be set by the control unit 2300. At this time, the direction of a wind blowing at the location of the moving device 2100 may be taken into account as well. Referring to FIG. 14, it may be anticipated that a northwest wind is blowing at the location 1 as well.

Although a location 3 is a location not included in the anticipated contamination map, the location 3 may be included in the moving route of the moving device 2100, and a contamination detecting operation may be performed at the location 3. As described above, since the anticipated contamination map is information anticipated based on limited information, the anticipated contamination map may not sufficiently reflect an actual situation. Therefore, the control unit 2300 may perform a contamination detecting operation for locations not included in the anticipated contamination map.

The locations for detecting a contamination and the moving route shown in FIG. 14 are merely examples. The moving device 2100 may continuously perform contamination detecting operations while moving along the moving route, and the moving device 2100 may be configured to detect a contamination in a largest range as possible by taking the maximum movable range of the moving device 2100 into account.

Meanwhile, the moving device 2100 may perform a contamination detecting operation configured by the control unit 2300 at the location 1. The contamination detecting operation may include operations for determining whether a location is contaminated, a type of a contaminant, and a degree of contamination. Likewise, the moving device 2100 may perform a contamination detecting operation at the locations 2 to 4 as well.

According to an embodiment of the present invention, the moving route of the moving device 2100 may be configured to be a closed loop route, where the control unit 2300 may further dispatch a new moving device other than a moving device already dispatched in the anticipated contamination region and configure a moving route of the new moving device to be a closed loop route.

For example, when the anticipated contamination map is generated and, as a contamination detecting operation by the moving device dispatched in the anticipated contamination region is completed, the contamination map is updated, the control unit 2300 may dispatch a new moving device by taking the updated contamination map (hereinafter referred to as a 'corrected contamination map') into account. At this time, a moving route of the new moving device may be a closed loop route including the anticipated contamination region and a reference location.

The reference location may be understood as a location where a moving device is stored before being dispatched in the anticipated contamination region. In FIG. 14, it is assumed that a location H corresponds to the reference location.

The control unit 2300 configures a moving route starting from the location H for the new moving device, where a contamination detecting region may determines at least one contamination detecting location by taking the corrected contamination map into account and configure a moving route including the at least one contamination detecting location. At this time, the moving route may be configured to a path starting from the reference location, passing through the at least one contamination detecting location, and returning back to the reference location.

Meanwhile, the closed loop moving route is not necessarily applied to a newly dispatched moving device only. The moving device initially dispatched in the anticipated contamination region may also return to the reference location. Therefore, a closed loop moving path including the reference location may also be configured for a moving device that is already dispatched.

Figure 15:
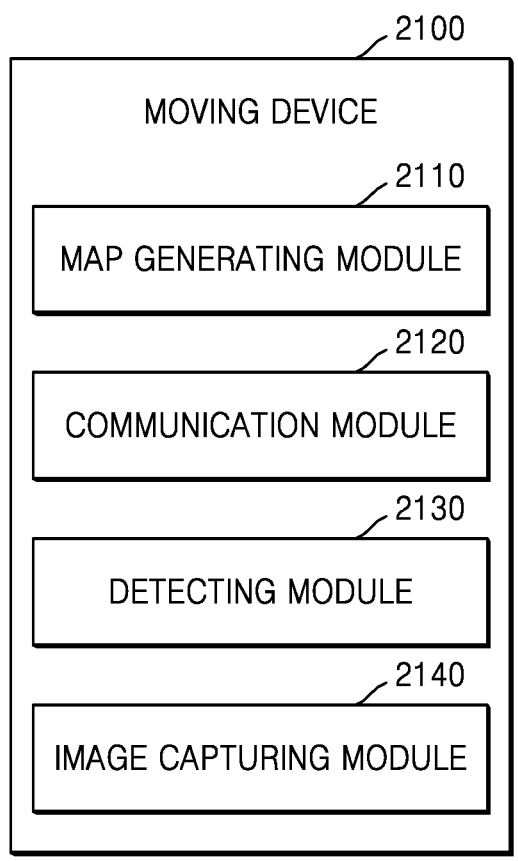
FIG. 15 is a schematic view of a configuration of a moving device according to an embodiment of the present invention.

FIG. 15 is a schematic view of a configuration of a moving device according to an embodiment of the present invention;

Referring to FIG. 15, the moving device 2100 according to an embodiment of the present invention includes the map generating module 2110, a communication module 2120, a detecting module 2130, and an image capturing module 2140. As described with reference to FIG. 11, the map generating module 2110 generates an anticipated contamination map for an anticipated contamination region by using a wind direction, a wind speed, and weather information.

The communication module 2120 transmits the anticipated contamination map generated by the map generating module 2110 to the outside or transmits an image obtained through the image capturing module 2140 to the outside. Furthermore, the communication module 2120 may transmit a contamination detecting result to the outside.

The detecting module 2130 exposes a detection sheet for detecting a contamination to the outside during a contamination detecting operation. Here, the contamination detecting result includes an image of the detection sheet obtained by using the image capturing module 2140.

Meanwhile, the moving device 2100 may capture an image of a projectile dropped in an anticipated contamination region, recognize a type and a size of the projectile, and transmit the recognized information to a map updating unit 2500 described above with reference to FIG. 11. More specifically, the moving device 2100 may be dispatched in the anticipated contamination region, capture an image of a dropped projectile by using the image capturing module 2140 at a location at which a contaminant is initially dropped, analyze the captured image, and recognize a type and a size of the projectile. The recognized information is transmitted to the map updating unit 2500 as described above and may be utilized for updating the anticipated contamination map. Alternatively, the recognized information may be provided to the map generating module 2110 and utilized for generating the anticipated contamination map.

Information obtained through a plurality of modules included in the moving device 2100 is necessary for generating accurate contamination information, and it may be understood that information generated by the moving device 2100 is transmitted to the map updating unit 2500.

Meanwhile, according to an embodiment of the present invention, the moving device 2100 may correspond to the moving device 100 for detecting contamination including the configuration described above with reference to FIGS. 1 to 9. In other words, the detecting module 2130 may include a sheet frame supporting shaft, a sheet frame unit, a cam gear unit, a rotating shaft, and a driving motor.

Furthermore, a rotating gear is installed on one side of the sheet frame unit, and teeth of the cam gear unit may engage with the rotating gear. Also, the sheet frame unit includes a plurality of sheet frames, the cam gear unit includes a plurality of cam gears, and the plurality of cam gears may be installed at pre-set angles along the rotating direction of the rotating shaft.

Furthermore, the detecting module 2130 may include a chamber unit having a plurality of chambers, and the sheet frame and the cam gear may be arranged in each of the chambers. Furthermore, the chamber may be provided with a sealing door, and the sealing door may be provided with a hinge structure.

Figure 16:
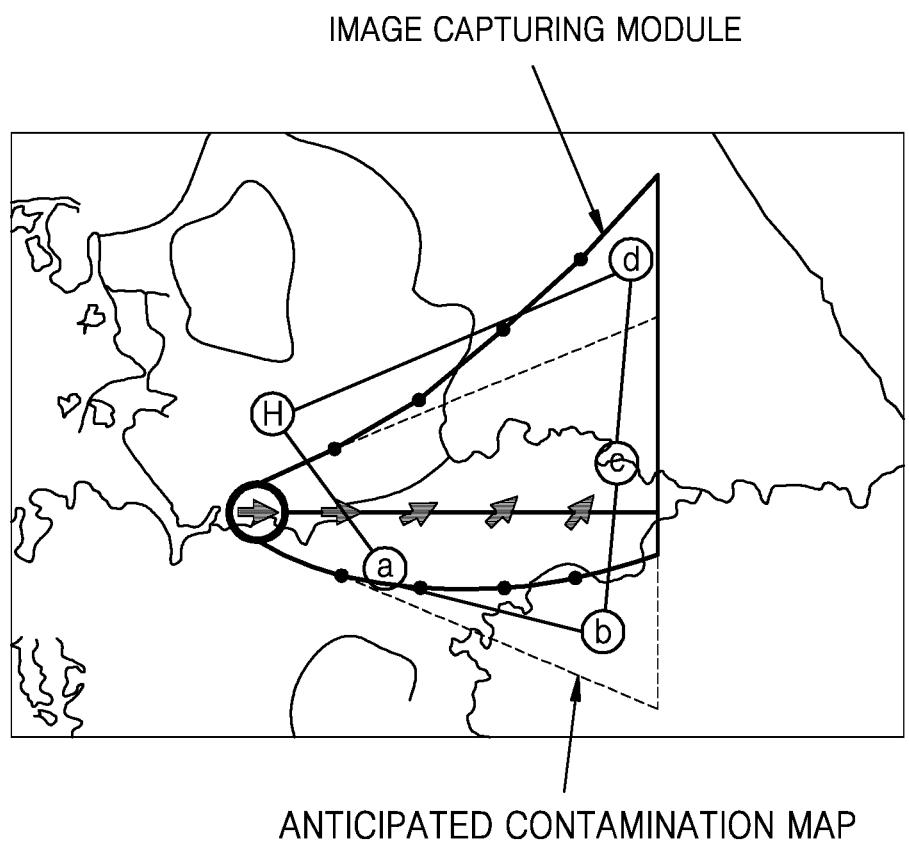
FIG. 16 is a diagram showing an updated corrected contamination map according to an embodiment of the present invention and a moving route of a moving device configured in correspondence thereto.

FIG. 16 is a diagram showing an updated corrected contamination map according to an embodiment of the present invention and a moving route of a moving device configured in correspondence thereto.

In FIG. 16, the map indicated by the dotted line corresponds to an anticipated contamination map, and the map indicated by the solid line corresponds to a corrected contamination map. The corrected contamination map is obtained as the map updating unit 1500 and 2500 described above with reference to FIGS. 10 and 11 updates the anticipated contamination map based on a result of detecting a contamination at a contamination detecting location determined by the control unit 1300 and 2300. The corrected contamination map reflects actual on-site contamination information.

Referring to FIG. 16, it may be seen that contaminants are not actually spreading in the lower region of the anticipated contamination map, whereas contaminants are spreading in the upper region unlike an initial anticipation. The anticipated contamination map is generated by using information, such as a wind direction and a wind speed, measured by a moving device at a location where a contaminant is initially dropped and anticipated information may not be accurate in a wide region.

Meanwhile, the control unit 1300 or 2300 may configure a new moving route of a moving device by taking the corrected contamination map into account. The newly configured moving route is to confirm information indicated in the corrected contamination map or to obtain new contamination information regarding previously omitted contamination detecting locations.

Referring to FIG. 16, the moving route is configured as a closed loop route including the reference location H and may be configured by taking the wind direction indicated by an arrow into account. The moving device starting from the reference location H passes through locations a to d and then returns to the reference location H and may perform contamination detecting operations at the locations a to d.

The map update unit 1500 or 2500 may receive results of the contamination detecting operations of the moving device and update the corrected contamination map again, and the operation may be repeatedly performed as needed.

Figure 17:
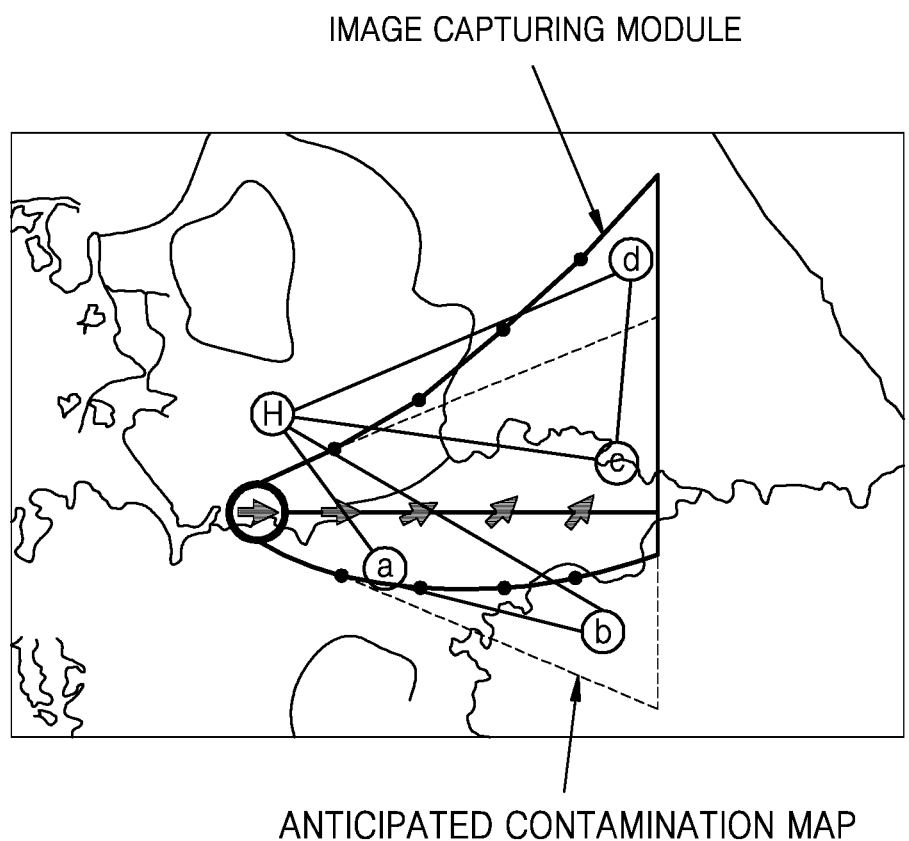
FIG. 17 is a diagram exemplifying moving routes configured for a plurality of moving devices.

FIG. 17 is a diagram exemplifying moving routes configured for a plurality of moving devices.

A plurality of moving devices may be used for contamination detecting system and method according to the present invention. FIG. 17 shows an example in which two moving devices (a first moving device and a second moving device) are used.

Referring to FIG. 17, a moving route (first moving route) including a reference location H, a location a, and a location b is configured for the first moving device, whereas a moving route (second moving route) including the reference location H, a location c, and a location d is configured for the second moving device.

Therefore, the first moving device moves along the first moving route, perform contamination detecting operations at the location a and the location b, and returns to the reference location H, whereas the second moving device moves along the second moving route, perform contamination detecting operations at the location c and the location d, and returns to the reference location H.

When configuring moving routes for a plurality of moving devices, it is necessary to prevent a collision between the moving devices and consider movable distances according to amounts of energy stored in the moving devices. Furthermore, different tasks may be assigned to moving devices having different moving routes. For example, the first moving device may be configured to perform a contamination detecting operation at a location not included in the corrected contamination map, whereas the second moving device may be configured to perform a contamination detecting operation at a location included in the corrected contamination map.

Alternatively, the first moving device and the second moving device may be configured to perform contamination detecting operations for different types of contaminants. For example, the first moving device may be configured to detect a contamination by a chemical gas, whereas the second moving device may be configured to detect a contamination by a nerve gas. Here, the first moving device and the second moving device may include different types of detection sheets.

Figure 18:
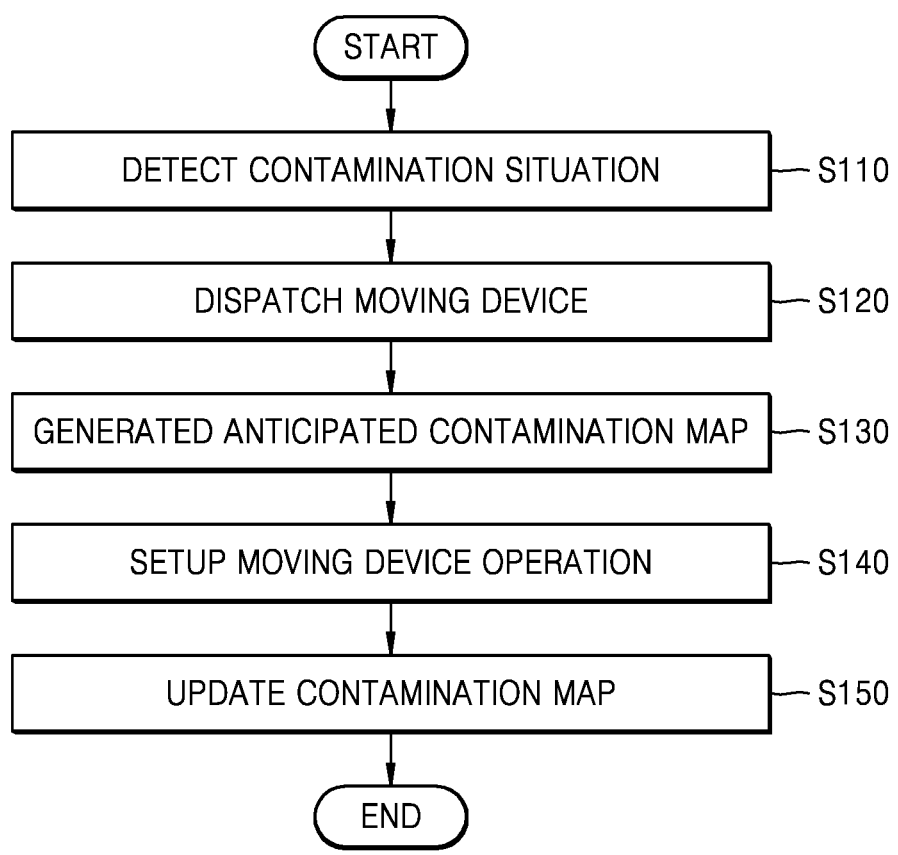
FIG. 18 is a schematic flowchart of a contamination detecting method according to an embodiment of the present invention.

FIG. 18 is a schematic flowchart of a contamination detecting method according to an embodiment of the present invention.

Referring to FIG. 18, a contamination detecting method according to an embodiment of the present invention is a method of detecting a contamination by using at least one moving device and includes a contamination situation detecting operation S110, a moving device dispatching operation S120, an anticipated contamination map generating operation S130, a moving device operation setup operation S140, and a contamination map updating operation S150.

In the contamination situation detecting operation S110, it is detected whether a contamination situation is occurring. A detecting operation performed here is an operation not for detecting whether an actual contamination situation is occurred, but for detecting whether a contamination situation is anticipated. For example, the detecting operation may be an operation for detecting whether an object assumed as a chemical projectile is dropped in a certain region or receiving an alarm or a notification received from the outside.

In the moving device dispatching operation S120, the moving device is dispatched in an anticipated contamination region in response to the occurrence of the contamination situation. When it is determined that the contamination situation is occurring, one moving device may be initially dispatched in the anticipated contamination region. The moving device refers to an unmanned device that performs a contamination detecting operation and may detect a hazardous situation occurring in a region difficult for a human to access. Meanwhile, the moving device may include a driving unit that enables movements on land, in the air, or in the water Meanwhile, in the moving device dispatching operation S120, the moving device may be located by designating a specific location in the anticipated contamination region and configuring a moving route, and an operation of the moving device at the designated location may be configured. The moving route may include a path from a starting point to a destination of the moving device and a path returning from the destination to the starting point.

At this time, the method may further include an operation for capturing an image of a projectile dropped in the anticipated contamination region, recognizing a type and a size of the projectile, and transmitting the recognized information. The moving device may include an image capturing module to obtain images of the surroundings, detect whether there is a projectile dropped around the designated location, obtain an image of a projectile by using the image capturing module when there is the projectile, and recognize a type and a size of the projectile.

Information recognized as described above may be utilized for generating a contamination map and may be utilized by a user to update a contamination map.

In the anticipated contamination map generating operation S130, the moving device generates an anticipated contamination map for the anticipated contamination region. When it is anticipated that an initial contamination situation is occurring, the moving device may not perform operations other than a moving operation until the moving device 1100 arrives at the designated location and, in the moving device dispatching operation (S120), the moving device may be configured to perform a contamination detecting operation to determine whether a contamination situation is actually occurring when the moving device arrives at the designated location (in the anticipated contamination region).

Meanwhile, the anticipated contamination map may include anticipated contamination information about a region in which occurrence of the contamination situation is anticipated and surrounding regions, and the anticipated contamination information may be generated in consideration of a type of a contamination material dropped into the anticipated contamination region and surrounding environments including terrain of the anticipated contamination region.

In the moving device operation setup operation S140, the anticipated contamination map is received from the moving device, a moving route of the moving device is configured in correspondence to the anticipated contamination map, and an operation of the moving device including a location for performing a contamination detecting operation is configured.

A moving device for an operation configuration in the moving device operation setup operation S140 may be a moving device that generated the anticipated contamination map or may be a newly dispatched moving device (e.g., a second moving device). When an operation is configured for the second moving device, the moving device that generated the anticipated contamination map may return to the starting location. Next, a moving route is configured for the second moving device to perform contamination detecting operations at a plurality of locations included in the anticipated contamination map, and locations for performing the contamination detecting operations are configured.

Also, the moving device may continuously measure wind directions and wind speeds while moving along the moving route. In the moving device operation setup operation S140, a moving route of the moving device may be configured in real time by taking wind direction information and the wind speed information transmitted from the moving device. In other words, the moving route configured in the moving device dispatching operation S120 may be changed.

After the anticipated contamination map is generated, in the moving device operation setup operation S140, an optimal moving route along which the moving device may efficiently move and perform contamination detecting operations may be generated.

In the contamination map updating operation S150, results of contamination detections are received from the moving device, and the anticipated contamination map is updated in correspondence to results of contamination detections.

The moving device may perform a pre-set contamination detecting operation at a contamination detecting location configured in the moving device operation setup operation S140 and transmit a result of the contamination detecting operation. Since the anticipated contamination map is anticipated information in which actual information is not reflected, the moving device may directly perform a contamination detecting operation and reflect a result of the operation, thereby generating a more accurate contamination map.

On the other hand, a result of a contamination detection by the moving device may be obtained through a detection sheet provided in the moving device, wherein the detection sheet has a characteristic of changing color or shape when exposed to a contamination situation.

The moving device may expose the detection sheet to the outside at a contamination detecting location to determine whether the location is contaminated, and a result of the contamination detection may include an image of the detection sheet captured by using an image capturing module.

In the contamination map updating operation S150, the anticipated contamination map is updated and a corrected contamination map is generated, wherein the corrected contamination map may provide information for performing an effective and safe decontaminating operation in a contamination region.

Figure 19:
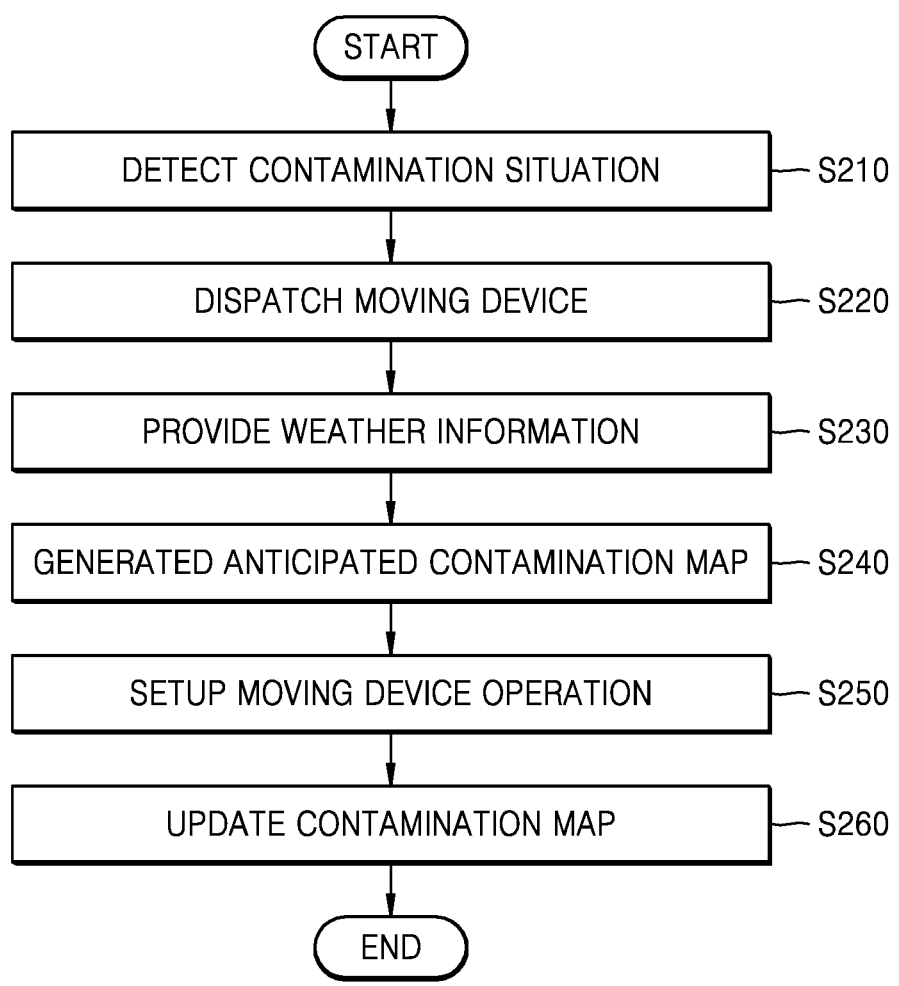
FIGS. 19 and 20 are schematic flowcharts of contamination detecting methods according to other embodiment of the present invention.
Figure 20:
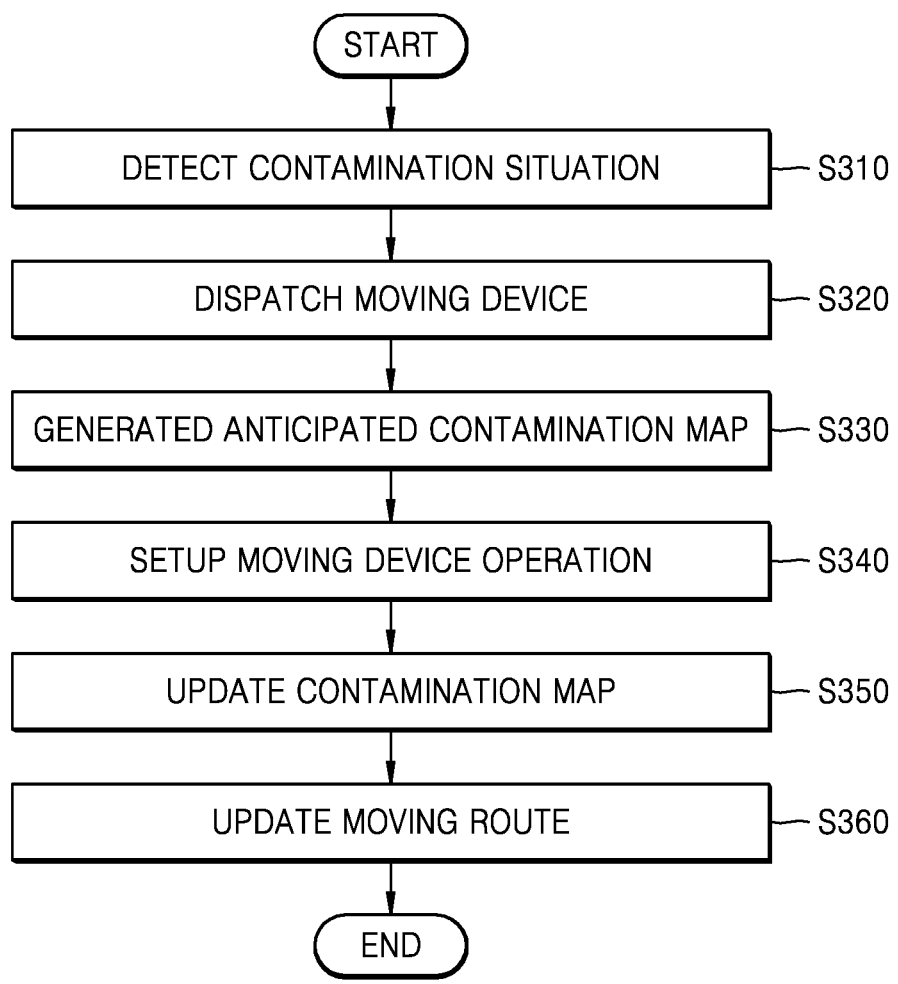

FIGS. 19 and 20 are schematic flowcharts of contamination detecting methods according to other embodiment of the present invention.

Referring to FIG. 19, a contamination detection method according to another embodiment of the present invention includes a contamination situation detecting operation S210, a moving device dispatching operation S220, a weather information providing operation S230, an anticipated contamination map generating operation S240, a moving device operation setup operation S250, and a contamination map updating operation S260.

In the weather information providing operation S230, weather information is provided to the moving device. The weather information is information about the anticipated contamination region. The moving device may generate the anticipated contamination map by using a wind direction and a wind speed measured in the anticipated contamination region and the weather information.

The weather information may include information like the temperature, the humidity, and the precipitation of the anticipated contamination region, and the moving device may analyze information directly measured by the moving device in the anticipated contamination region, such as a wind direction and a wind speed, and the weather information and calculate a direction, a range, and/or a speed at which contaminants in the anticipated contamination region are anticipated to spread.

The information calculated as described above is utilized for updating the anticipated contamination map in the contamination map updating operation S260.

Referring to FIG. 20, a contamination detection method according to another embodiment of the present invention includes a contamination situation detecting operation S310, a moving device dispatching operation S320, an anticipated contamination map generation operation S330, a moving device operation setup operation S340, a contamination map updating operation S350, and a moving route updating operation S360.

In the moving route updating operation S360, a moving route of the moving device is updated by taking the updated anticipated contamination map (corrected contamination map) into account. At this time, the moving route to be updated may be a closed loop route including a reference location. Here, the reference location refers to a location at which the moving device initially starts.

When the corrected contamination map is generated, a new moving route may be configured to the moving device dispatched in the contamination region in the moving route updating operation S360. Here, the newly configured moving route may include a location anticipated as being omitted by the moving device or a location at which a contamination situation is anticipated as being solved according to the lapse of time.

Furthermore, since the moving device dispatched in the contamination region needs to return to the reference location, the moving route may be configured as a closed loop route including the reference location.

Embodiments according to the present invention described above can be implemented in the form of a computer program that can be executed on various components on a computer, and such a computer program can be recorded on a computer-readable medium. Here, the medium may be a magnetic medium such as a hard disk, a floppy disk and a magnetic tape, an optical recording medium such as CD-ROM and DVD, a magneto-optical medium such as a floptical disk, or a hardware device specifically configured to store and execute program instructions such as a ROM, a RAM, or a flash memory.

Meanwhile, the computer program may be designed and configured specifically for present invention or may be one available to one of ordinary skill in the computer software field. Examples of computer programs may include not only machine language codes such as those produced by a compiler, but also high-level language codes that may be executed by a computer by using an interpreter or the like.

The particular embodiments described in the present invention are merely examples and are not intended to limit the scope of the present invention in any manner. For clarity of description, descriptions of conventional electronic configurations, control systems, software, and other functional aspects of such systems may be omitted. Also, connections of lines or connection members between the components shown in the drawings are examples of functional connections and/or physical or circuit-wise connections, which may be indicated in an actual device as various replaceable or additional functional connections, physical connections, or circuit-wise connections. Also, unless stated specifically such as "essential" and "important", it may not be a necessary component for the application of the present invention.

Accordingly, the technical spirit of the present invention should not be limited to the above-described embodiments, and not only the scope of the claims of the present invention, but also all scopes that are equivalent to or equivalently desired from the following claims are within the technical spirit of the present invention.

INDUSTRIAL APPLICABILITY

Embodiments of the present invention relate to a moving device for detecting contamination, a contamination detecting system, a contamination detecting method, and a computer-readable recording medium, and more particularly, to a moving device capable of detecting a chemical substance, and a contamination detecting system, a contamination detecting method, and a computer-readable recording medium for performing contamination detections by using the moving device, generating a contamination map based on results of the contamination detections, and continuously updating the contamination map, thereby preventing human from being exposed to contaminants.

The invention claimed is:

1. A contamination detecting system comprising:
a moving device;
a monitoring unit configured to detect whether a contamination situation is anticipated;
a control unit configured to dispatch the moving device in an anticipated contaminated region in response to the monitoring unit detecting that the contamination situation is anticipated, configure a moving route of the moving device, and control a contamination detecting operation of the moving device;
a map receiving unit configured to receive an anticipated contamination map for the anticipated contamination region from the moving device; and
a map updating unit configured to receive a contamination detection result of the moving device in a region corresponding to the anticipated contamination map and update the anticipated contamination map in correspondence thereto,
wherein the moving device is configured to capture an image of a projectile dropped in the anticipated contamination region, recognize a type and a size of the projectile, and transmit recognized information about the projectile to the map updating unit, and
wherein the map updating unit, that is separate from the moving device, is configured to update the anticipated contamination map based on the recognized information about the projectile.

2. The contamination detecting system of claim 1, further comprising
a weather information providing unit for providing weather information to the moving device,
wherein the moving device comprises a map generating module configured to generate the anticipated contamination map by using a wind direction and a wind speed measured in the anticipated contaminated region and the weather information.

3. The contamination detecting system of claim 1, wherein
the control unit configures a moving route of the moving device by taking a wind direction in the anticipated contamination region into account for the moving device to move along the wind direction and controls a contamination detecting operation of the moving device on the moving route.

4. The contamination detecting system of claim 1, wherein
the control unit configures a contamination detecting location of the moving device by taking a wind direction on the moving route of the moving device into account.

5. The contamination detecting system of claim 1, wherein
the control unit configures the moving route of the moving device by taking a contamination map updated by the map updating unit into account, and the moving route is configured as a closed loop route including a reference location.

6. The contamination detecting system of claim 1, wherein
the control unit dispatches a plurality of moving devices in the anticipated contamination region and configures a moving route for each of the plurality of moving devices by taking a movable distance of each of the plurality of moving devices or a task assigned to each of the plurality of moving devices into account.

7. The contamination detecting system of claim 1, wherein
the moving device comprises:
a communication module configured to transmit a result of the contamination detection;
a detecting module configured to expose a detection sheet for detecting a contamination to an outside of the moving device; and
an image capturing module,
wherein the result of the contamination detection includes an image of the detection sheet obtained by using the image capturing module.

8. A method of contamination detection, the method comprising:
detecting whether a contamination situation is anticipated;
dispatching a moving device in an anticipated contamination region in response to detecting that the contamination situation is anticipated;
generating, by the moving device, an anticipated contamination map for the anticipated contamination region;
receiving the anticipated contamination map from the moving device, configuring a moving route of the moving device in correspondence to the anticipated contamination map, and configuring an operation of the moving device including a contamination detection location;
receiving a contamination detection result from the moving device and updating, by a map updating unit that is separate from the moving device, the anticipated contamination map in correspondence to the contamination detection result; and
by the moving device:
capturing an image of a projectile dropped in the anticipated contamination region, recognizing a type and a size of the projectile, and transmitting recognized information about the projectile to the map updating unit,
wherein the updating comprises updating, by the map updating unit that is separate from the moving device, the anticipated contamination map based on the recognized information about the projectile.

9. The method of claim 8, further comprising
providing weather information to the moving device,
wherein, in the generating of the anticipated contamination map, the anticipated contamination map is generated by the moving device using a wind direction and a wind speed measured by the moving device in the anticipated contamination region and the weather information.

10. The method of claim 8, wherein,
in the configuring of the operation of the moving device, a moving route of the moving device is configured by taking a wind direction in the anticipated contamination region into account for the moving device to move along the wind direction and a contamination detecting operation of the moving device on the moving route are configured.

11. The method of claim 8, wherein,
in the configuring of the operation of the moving device,
contamination detecting locations of the moving device are configured by taking the wind direction on the moving route of the moving device into account.

12. The method of claim 8, further comprising
updating the moving route of the moving device by taking an updated anticipated contamination map into account,
wherein the moving route is configured as a closed loop route including a reference location.

13. The method of claim 8, wherein,
in the dispatching of the moving device, a plurality of moving devices are dispatched in the anticipated contamination region, and
in the configuring of the operation of the moving device, a moving route for each of the plurality of moving devices is configured by taking a movable distance of each of the plurality of moving devices or a task assigned to each of the plurality of moving devices into account.

14. The method of claim 8, wherein
the contamination detection result comprises an image of a detection sheet for the detecting provided on the moving device, the image taken by the moving device using an imaging capturing module.

15. A computer-readable recording medium on which a program for performing the method according to claim 8 is recorded.

* * * * *